US012635938B2

(12) United States Patent (10) Patent No.: US 12,635,938 B2
Addison et al. (45) Date of Patent: May 26, 2026

(54) MONITORING FOR SLEEP APNEA USING NON-CONTACT MONITORING SYSTEM AND PULSE OXIMETRY SYSTEM

(71) Applicant: Covidien LP, Mansfield, MA (US)

(72) Inventors: Paul S. Addison, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 322 days.

(21) Appl. No.: 18/466,755

(22) Filed: Sep. 13, 2023

(65) Prior Publication Data

US 2024/0188882 A1      Jun. 13, 2024

Related U.S. Application Data

(60) Provisional application No. 63/386,421, filed on Dec. 7, 2022.

(51) Int. Cl.
| | |
|---|---|
| *A61B 5/1455* | (2006.01) |
| *A61B 5/00* | (2006.01) |
| *A61B 5/08* | (2006.01) |

(52) U.S. Cl.
CPC .......... *A61B 5/4818* (2013.01); *A61B 5/0816* (2013.01); *A61B 5/14551* (2013.01); *A61B 5/7264* (2013.01)

(58) Field of Classification Search
CPC ... A61B 5/4818; A61B 5/0816; A61B 5/1455; A61B 5/14551; A61B 5/7264
See application file for complete search history.

(56) References Cited

U.S. PATENT DOCUMENTS

| | | | |
|---|---|---|---|
| 5,107,845 | A | 4/1992 | Guern et al. |
| 5,408,998 | A | 4/1995 | Mersch |
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,241,684 | B1 | 6/2001 | Amano et al. |

(Continued)

FOREIGN PATENT DOCUMENTS

| | | |
|---|---|---|
| CA | 2234191 A1 | 10/1998 |
| CN | 106725410 A | 5/2017 |

(Continued)

OTHER PUBLICATIONS

Sokooti, Hess , et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

(Continued)

*Primary Examiner* — Eric F Winakur

(74) *Attorney, Agent, or Firm* — Dymera IP, LLC

(57) ABSTRACT

A system for detecting and identifying sleep apnea, such as obstructive sleep apnea, that includes a non-contact patient monitoring system and a pulse oximetry system. The methods utilize respiratory parameters (e.g., respiration rate, respiration volume) from the non-contact patient monitoring system to determine a significant reduction in or absence of the patient's respiration. The methods also utilize cardiological information (e.g., pulse) from a pulse oximetry system to determine intrathoracic pressure increases from various modulations of the PPG signal during the patient's respiration cycle.

20 Claims, 12 Drawing Sheets

(56) References Cited

U.S. PATENT DOCUMENTS

| | | | |
|---|---|---|---|
| 6,668,071 B1 | 12/2003 | Minkin et al. | |
| 6,920,236 B2 | 7/2005 | Prokoski | |
| 6,980,679 B2 * | 12/2005 | Jeung ................... | A61B 5/4818 |
| | | | 600/534 |
| 7,431,700 B2 | 10/2008 | Aoki et al. | |
| 7,558,618 B1 | 7/2009 | Williams | |
| 8,149,273 B2 | 4/2012 | Liu et al. | |
| 8,754,772 B2 | 6/2014 | Horng et al. | |
| 8,792,969 B2 | 7/2014 | Bernal et al. | |
| 8,971,985 B2 | 3/2015 | Bernal et al. | |
| 9,226,691 B2 | 1/2016 | Bernal et al. | |
| 9,282,725 B2 | 3/2016 | Jensen-Jarolim et al. | |
| 9,301,710 B2 | 4/2016 | Mestha et al. | |
| 9,402,601 B1 | 8/2016 | Berger et al. | |
| 9,436,984 B2 | 9/2016 | Xu et al. | |
| 9,443,289 B2 | 9/2016 | Xu et al. | |
| 9,504,426 B2 | 11/2016 | Kyal et al. | |
| 9,508,141 B2 | 11/2016 | Khachaturian et al. | |
| 9,607,138 B1 | 3/2017 | Baldwin et al. | |
| 9,662,022 B2 | 5/2017 | Kyal et al. | |
| 9,693,693 B2 | 7/2017 | Farag et al. | |
| 9,693,710 B2 | 7/2017 | Mestha et al. | |
| 9,697,599 B2 | 7/2017 | Prasad et al. | |
| 9,750,461 B1 | 9/2017 | Telfort | |
| 9,839,756 B2 | 12/2017 | Klasek | |
| 9,943,371 B2 | 4/2018 | Bresch et al. | |
| 10,213,540 B2 | 2/2019 | Burbank et al. | |
| 10,278,585 B2 | 5/2019 | Ferguson et al. | |
| 10,376,147 B2 | 8/2019 | Wood et al. | |
| 10,398,353 B2 | 9/2019 | Addison et al. | |
| 10,447,972 B2 | 10/2019 | Patil | |
| 10,489,912 B1 | 11/2019 | Brailovskiy | |
| 10,523,852 B2 | 12/2019 | Tzvieli et al. | |
| 10,588,779 B2 | 3/2020 | Vorhees et al. | |
| 10,589,916 B2 | 3/2020 | Mcrae | |
| 10,650,585 B2 | 5/2020 | Kiely | |
| 10,667,723 B2 | 6/2020 | Jacquel et al. | |
| 10,702,188 B2 | 7/2020 | Addison et al. | |
| 10,729,357 B2 | 8/2020 | Larson et al. | |
| 10,874,331 B2 | 12/2020 | Kaiser et al. | |
| 10,937,296 B1 | 3/2021 | Kukreja et al. | |
| 10,939,824 B2 | 3/2021 | Addison et al. | |
| 10,939,834 B2 | 3/2021 | Khwaja et al. | |
| 10,966,059 B1 | 3/2021 | Dayal et al. | |
| 11,311,252 B2 | 4/2022 | Jacquel et al. | |
| 11,315,275 B2 | 4/2022 | Addison et al. | |
| 11,317,828 B2 | 5/2022 | Addison et al. | |
| 11,350,850 B2 | 6/2022 | Jacquel et al. | |
| 11,850,026 B2 | 12/2023 | Levi et al. | |
| 2002/0137464 A1 | 9/2002 | Dolgonos et al. | |
| 2004/0001633 A1 | 1/2004 | Caviedes | |
| 2004/0258285 A1 | 12/2004 | Hansen et al. | |
| 2005/0203348 A1 | 9/2005 | Shihadeh et al. | |
| 2007/0116328 A1 | 5/2007 | Sablak et al. | |
| 2008/0001735 A1 | 1/2008 | Tran | |
| 2008/0108880 A1 | 5/2008 | Young et al. | |
| 2008/0279420 A1 | 11/2008 | Masticola et al. | |
| 2008/0295837 A1 | 12/2008 | McCormick et al. | |
| 2009/0024012 A1 | 1/2009 | Li et al. | |
| 2009/0141124 A1 | 6/2009 | Liu et al. | |
| 2009/0304280 A1 | 12/2009 | Aharoni et al. | |
| 2010/0210924 A1 | 8/2010 | Parthasarathy et al. | |
| 2010/0236553 A1 | 9/2010 | Jafari et al. | |
| 2010/0249630 A1 | 9/2010 | Droitcour et al. | |
| 2010/0324437 A1 | 12/2010 | Freeman et al. | |
| 2011/0144517 A1 | 6/2011 | Cervantes | |
| 2011/0150274 A1 | 6/2011 | Patwardhan et al. | |
| 2012/0065533 A1 | 3/2012 | Carrillo et al. | |
| 2012/0075464 A1 | 3/2012 | Derenne et al. | |
| 2012/0195473 A1 | 8/2012 | De Haan et al. | |
| 2012/0243797 A1 | 9/2012 | Di Venuto Dayer et al. | |
| 2013/0073312 A1 | 3/2013 | Thompson et al. | |
| 2013/0267873 A1 | 10/2013 | Fuchs | |
| 2013/0271591 A1 | 10/2013 | Van Leest et al. | |
| 2013/0272393 A1 | 10/2013 | Kirenko et al. | |
| 2013/0275873 A1 | 10/2013 | Shaw et al. | |
| 2013/0324830 A1 | 12/2013 | Bernal et al. | |
| 2013/0324876 A1 | 12/2013 | Bernal et al. | |
| 2014/0023235 A1 | 1/2014 | Cennini et al. | |
| 2014/0052006 A1 | 2/2014 | Lee et al. | |
| 2014/0053840 A1 | 2/2014 | Liu | |
| 2014/0073860 A1 | 3/2014 | Urtti | |
| 2014/0139405 A1 | 5/2014 | Ribble et al. | |
| 2014/0140592 A1 | 5/2014 | Lasenby et al. | |
| 2014/0235976 A1 | 8/2014 | Bresch et al. | |
| 2014/0267718 A1 | 9/2014 | Govro et al. | |
| 2014/0272860 A1 | 9/2014 | Peterson et al. | |
| 2014/0275832 A1 | 9/2014 | Muehlsteff et al. | |
| 2014/0276104 A1 | 9/2014 | Tao et al. | |
| 2014/0330336 A1 | 11/2014 | Errico et al. | |
| 2014/0334697 A1 | 11/2014 | Kersten et al. | |
| 2014/0358017 A1 | 12/2014 | Op Den Buijs et al. | |
| 2014/0378810 A1 | 12/2014 | Davis et al. | |
| 2014/0379369 A1 | 12/2014 | Kokovidis et al. | |
| 2015/0003723 A1 | 1/2015 | Huang et al. | |
| 2015/0068069 A1 | 3/2015 | Tran et al. | |
| 2015/0094597 A1 | 4/2015 | Mestha et al. | |
| 2015/0131880 A1 | 5/2015 | Wang et al. | |
| 2015/0157269 A1 | 6/2015 | Lisogurski et al. | |
| 2015/0190088 A1 * | 7/2015 | Chen ................... | A61B 5/4818 |
| | | | 600/301 |
| 2015/0198707 A1 | 7/2015 | Al-Alusi | |
| 2015/0223731 A1 | 8/2015 | Sahin | |
| 2015/0238150 A1 | 8/2015 | Subramaniam | |
| 2015/0265187 A1 | 9/2015 | Bernal et al. | |
| 2015/0282724 A1 | 10/2015 | Mcduff et al. | |
| 2015/0286779 A1 | 10/2015 | Bala et al. | |
| 2015/0301590 A1 | 10/2015 | Furst et al. | |
| 2015/0317814 A1 | 11/2015 | Johnston et al. | |
| 2015/0379370 A1 | 12/2015 | Clifton et al. | |
| 2016/0000335 A1 | 1/2016 | Khachaturian et al. | |
| 2016/0049094 A1 | 2/2016 | Gupta et al. | |
| 2016/0082222 A1 | 3/2016 | Garcia Molina et al. | |
| 2016/0140828 A1 | 5/2016 | Deforest | |
| 2016/0143598 A1 | 5/2016 | Rusin et al. | |
| 2016/0151022 A1 | 6/2016 | Berlin et al. | |
| 2016/0156835 A1 | 6/2016 | Ogasawara et al. | |
| 2016/0174887 A1 | 6/2016 | Kirenko et al. | |
| 2016/0210747 A1 | 7/2016 | Hay et al. | |
| 2016/0235344 A1 | 8/2016 | Auerbach | |
| 2016/0310084 A1 | 10/2016 | Banerjee et al. | |
| 2016/0317041 A1 | 11/2016 | Porges et al. | |
| 2016/0345931 A1 | 12/2016 | Xu et al. | |
| 2016/0367186 A1 | 12/2016 | Freeman et al. | |
| 2017/0007342 A1 | 1/2017 | Kasai et al. | |
| 2017/0007795 A1 | 1/2017 | Pedro et al. | |
| 2017/0055877 A1 | 3/2017 | Niemeyer | |
| 2017/0065484 A1 | 3/2017 | Addison et al. | |
| 2017/0071516 A1 | 3/2017 | Bhagat et al. | |
| 2017/0095215 A1 | 4/2017 | Watson et al. | |
| 2017/0095217 A1 | 4/2017 | Hubert et al. | |
| 2017/0119340 A1 | 5/2017 | Nakai et al. | |
| 2017/0147772 A1 | 5/2017 | Meehan et al. | |
| 2017/0164904 A1 | 6/2017 | Kirenko | |
| 2017/0172434 A1 | 6/2017 | Amelard et al. | |
| 2017/0173262 A1 | 6/2017 | Veltz | |
| 2017/0238805 A1 | 8/2017 | Addison et al. | |
| 2017/0238842 A1 | 8/2017 | Jacquel et al. | |
| 2017/0311887 A1 | 11/2017 | Leussler et al. | |
| 2017/0319114 A1 | 11/2017 | Kaestle | |
| 2018/0042486 A1 | 2/2018 | Yoshizawa et al. | |
| 2018/0042500 A1 | 2/2018 | Liao et al. | |
| 2018/0049669 A1 | 2/2018 | Vu et al. | |
| 2018/0053392 A1 | 2/2018 | White et al. | |
| 2018/0104426 A1 | 4/2018 | Oldfield et al. | |
| 2018/0106897 A1 | 4/2018 | Shouldice et al. | |
| 2018/0169361 A1 | 6/2018 | Dennis et al. | |
| 2018/0217660 A1 | 8/2018 | Dayal et al. | |
| 2018/0228381 A1 | 8/2018 | Leboeuf et al. | |
| 2018/0303351 A1 | 10/2018 | Mestha et al. | |
| 2018/0310844 A1 | 11/2018 | Tezuka et al. | |
| 2018/0325420 A1 | 11/2018 | Gigi | |
| 2018/0333050 A1 | 11/2018 | Greiner et al. | |
| 2018/0333102 A1 | 11/2018 | De Haan et al. | |

(56) References Cited

U.S. PATENT DOCUMENTS

| | | | |
|---|---|---|---|
| 2018/0352150 A1 | 12/2018 | Purwar et al. |
| 2019/0050985 A1 | 2/2019 | Den Brinker et al. |
| 2019/0133499 A1 | 5/2019 | Auerbach |
| 2019/0142274 A1 | 5/2019 | Addison et al. |
| 2019/0199970 A1 | 6/2019 | Greiner et al. |
| 2019/0209046 A1 | 7/2019 | Addison et al. |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0187827 A1 | 6/2020 | Addison et al. |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0279464 A1 | 9/2020 | Llewelyn |
| 2020/0289024 A1 | 9/2020 | Addison et al. |
| 2020/0329976 A1 | 10/2020 | Chen et al. |
| 2020/0409383 A1 | 12/2020 | Maunder |
| 2021/0068670 A1 | 3/2021 | Redtel |
| 2021/0142874 A1 | 5/2021 | Llewelyn |
| 2021/0153746 A1 | 5/2021 | Addison et al. |
| 2021/0201517 A1 | 7/2021 | Yang et al. |
| 2021/0233631 A1 | 7/2021 | Llewelyn |
| 2021/0235992 A1 | 8/2021 | Addison |
| 2021/0295662 A1 | 9/2021 | Bugbee et al. |
| 2021/0313075 A1 | 10/2021 | Mc Namara et al. |
| 2022/0211296 A1 | 7/2022 | Addison et al. |
| 2023/0122367 A1 | 4/2023 | Tesar |

FOREIGN PATENT DOCUMENTS

| | | | |
|---|---|---|---|
| CN | 111728602 A | 10/2020 |
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2004173010 A | 6/2004 |
| JP | 2004283373 A | 10/2004 |
| JP | 3744778 B2 | 12/2005 |
| JP | 2009544080 A | 12/2009 |
| JP | 2011130996 A | 7/2011 |
| KR | 101644843 B1 | 8/2016 |
| RS | 20120373 A1 | 4/2014 |
| WO | 2004100067 A2 | 11/2004 |
| WO | 2005079658 A2 | 9/2005 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017100188 A2 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

"European Search Report", European Application No. 17156334.9, Applicant: Covidien LP, Aug. 23, 2017, 10 pages.

"European Search Report", European Patent Application No. 17156337. 2, Applicant: Covidien LP, Aug. 23, 2017, 10 pages.

"International Search Report and Written Opinion", International Application No. PCT/US2021/015669, Apr. 12, 2021, 15 pages.

"International Search Report and Written Opinion", International Application No. PCT/US2018/060648, Jan. 28, 2019, 17 pages.

"International Search Report and Written Opinion", International Application No. PCT/US2018/065492, Mar. 8, 2019, 12 pages.

"International Search Report and Written Opinion", International Application No. PCT/US2019/035433, Nov. 11, 2019, 17 pages.

"International Search Report and Written Opinion", International Application No. PCT/US2019/045600, Oct. 23, 2019, 19 pages.

"Invitation to Pay Additional Fees and Partial International Search Report", International Application No. PCT/US2019/035433, Sep. 13, 2019, 16 pages.

"Medical Electrical Equipment, Part 2-61: Particular requirements for basic safety and essential performance of pulse oximeter equipment", BSI Standards Publication, BS EN ISO 80601-2-61, 2011, 98 pages.

Aarts, Lonneke A.M., et al., "Non-contact heart rate monitoring utilizing camera photoplethysmography in neonatal intensive care unit-A Pilot Study", Early Human Development 89, 2013, pp. 943-948, 6 pages.

Abbas, A.K. , et al., "Neonatal non-contact respiratory monitoring based on real-time infrared thermography", Biomed. Eng. Online, vol. 10, No. 93, 2011, 17 pages.

Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.

Addison, Paul S., et al., "Developing an algorithm for pulse oximetry derived respirator rate (RRoxi): a healthy volunteer study", J Clin comput, No. 26, 2012, pp. 45-51, 7 pages.

Addison, Paul S., et al., "Pulse oximetry-derived respiratory rate in general care floor patients", J. Clin Monit Comput, No. 29, 2015, pp. 113-120, 8 pages.

Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.

Al-Naji, Ali , et al., "Real Time Apnoea Monitoring of Children Using the Microsoft Kinect Sensor: A Pilot Study", Sensors, 17(286), Feb. 3, 2017, 15 pages.

Amazon , "Dockem Koala Tablet Wall Mount Dock for ipad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.

Amelard , et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.

Armanian, A. M. , "Caffeine administration to prevent apnea in very premature infants", Pediatrics & Neonatology, 57 (5), 2016, pp. 408-412, 5 pages.

Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.

Barone, S , et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.

Bartula, M. , et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.

Bhattacharya, S. , et al., "A Novel Classification Method for Predicting Acute Hypotensive Episodes in Critical Care", 5th ACM Conference on Bioinformatics, Computational Bilogy and Health

(56) References Cited

OTHER PUBLICATIONS

Informatics (ACM-BCB 2014), Newport Beach, USA, 2014, 10 pages.

Bhattacharya, S. , et al., "Unsupervised learning using Gaussian Mixture Copula models", 21st International Conference on Computational Statistics (COMPSTAT 2014), Geneva, Switzerland, 2014, pp. 523-530, 8 pages.

Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.

Bousefsaf, Frederic , et al., "Continuous wavelet filtering on webcam photoplethysmographic signals to remotely assess the instantaneous heart rate", Biomedical Signal Processing and Control 8, 2013, pp. 568-574, 7 pages.

Bruser, C. , et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.

Cennini, Giovanni , et al., "Heart rate monitoring via remote photoplethysmography with motion artifacts reduction", Optics Express, vol. 18, No. 5, Mar. 1, 2010, pp. 4867-4875, 9 pages.

Colantonio, S. , et al., "A smart mirror to promote a healthy lifestyle", Biosystems Engineering. vol. 138, Innovations in Medicine and Healthcare, Oct. 2015, pp. 33-43, 11 pages.

Cooley , et al., "An Alorithm for the Machine Calculation of Complex Fourier Series", Aug. 17, 1964, pp. 297-301, 5 pages.

Di Fiore, J.M. , et al., "Intermittent hypoxemia and oxidative stress in preterm infants", Respiratory Physiology & Neurobiology, No. 266, 2019, pp. 121-129, 25 pages.

Fei, J. , et al., "Thermistor at a distance: unobtrusive measurement of breathing", IEEE Transactions on Biomedical Engineering, vol. 57, No. 4, 2010, pp. 968-998, 11 pages.

Feng, Litong , et al., "Dynamic ROI based on K-means for remote photoplethysmography", IEE International Conference on Accoustics, Speech and Signal Processing (ICASSP), Apr. 2015, pp. 1310-1314, 5 pages.

Fischer , et al., "ReMoteCare: Health Monitoring with Streaming Video", OCMB '08, 7th International Conference on Mobile Business, IEEE, Piscataway, NJ,, Jul. 7, 2008, pp. 280-286.

George , et al., "Respiratory Rate Measurement From PPG Signal Using Smart Fusion Technique", International Conference on Engineering Trends and Science & Humanities (ICETSH-2015), 2015, 5 pages.

Goldman, L.J. , "Nasal airflow and thoracoabdominal motion in children using infrared thermographic video processing", Pediatric Pulmonology, vol. 47, No. 5, 2012, pp. 476-486, 11 pages.

Grimm, T. , et al., "Sleep position classification from a depth camera using bed aligned maps", 23rd International Conference on Pattern Recognition (ICPR), Dec. 2016, pp. 319-324, 6 pages.

Gsmarena , "Apple iPad Pro 11 (2018)", https://www.gsmarena.com/apple_ipad_pro_11_(2018)-9386.pjp, viewed on Nov. 16, 2021, 1 page.

Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.

Han, J. , et al., "Visible and infrared image registration in man-made environments employing hybrid visuals features", Pattern Recognition Letters, vol. 34, No. 1, 2013, pp. 42-51, 10 pages.

Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.

Huddar, V. , et al., "Predicting Postoperative Acute Respiratory Failure in Critical Care using Nursing Notes and Physiological Signals", 36th Annual International Conference of IEEE Engineering in Medicine and Biology Society (IEEE Embc 2014), Chicago, USA, 2014, pp. 2702-2705, 4 pages.

Hyvarinen, A. , et al., "Independent Component Analysis: Algorithms and Applications", Neural Networks, vol. 13, No. 4, 2000, pp. 411-430, 31 pages.

Javadi, M. , et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M. , et al., "Non-invasive skin oxygenation imaging using a multi-spectral camera system: Effectiveness of various concentration algorithms applied on human skin", Proc. of SPIE, vol. 7174 717408-1, 2009, 14 pages.

Kong, Lingqin , et al., "Non-contact detection of oxygen saturation based on visible light imaging device using ambient light", Optics Express, vol. 21, No. 15, Jul. 29, 2013, pp. 17646-17471, 8 pages.

Kortelainen, J.M. , et al., "Sleep staging based on signals acquired through bed sensor", IEEE Transactions on Informational Technology in Biomedicine, vol. 14, No. 3, May 2010, pp. 776-785, 10 pages.

Kumar, M. , et al., "Distance PPG: Robust non-contact vital signs monitoring using a camera", Biomedical Optics Express, vol. 6, No. 5, May 1, 2015, 24 pages.

Kwon, Sungjun , et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.

Lai, C.J. , et al., "Heated humidified high-flow nasal oxygen prevents intraoperative body temperature decrease in non-intubated thoracoscopy", Journal of Anesthesia, Oct. 15, 2018, 8 pages.

Lawrence, E. , et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.

Li , et al., "A Non-Contact Vision-Based System for Respiratory Rate Estimation", IEEE 978-1-4244-7929-0/14, 2014, pp. 2119-2122, 4 pages.

Liu, H. , et al., "A Novel Method Based on Two Cameras for Accurate Estimation of Arterial Oxygen Saturation", BioMedical Engineering Online, vol. 14, No. 52, 2015, 18 pages.

Liu, S. , et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C. , et al., "Motion Magnification", ACM Transactions on Graphics (TOG), vol. 24, No. 3, 2005, pp. 519-526, 8 pages.

Lv, et al., "Class Energy Image Analysis for Video Sensor-Based Gait Recognition: A Review", Sensors, No. 15, 2015, pp. 932-964, 33 pages.

Mcduff, Daniel J., et al., "A Survey of Remote Optical Photoplethysmographic Imaging Methods", IEEE 987-1-4244-0270-1/15, 2015, pp. 6398-6404, 7 pages.

Mestha, L.K. , et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Mukherjee, S. , et al., "Patient health management system using e-health monitoring architecture", IEEE, International Advance Computing Conference (IACC), 978-1-4799-2572-8/14, Feb. 21, 2014, pp. 400-405, 6 pages.

Nguyen , et al., "3D shape, deformation and vibration measurements using infrared Kinect sensors and digital image correlation", Applied Optics, vol. 56, No. 32, Nov. 10, 2017, 8 pages.

Ni , et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar , et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

(56)            References Cited

OTHER PUBLICATIONS

Pereira, C., et al., "Noncontact Monitoring of Respiratory Rate in Newborn Infants Using Thermal Imaging", IEEE Transactions on Biomedical Engineering, Aug. 23, 2018, 10 pages.

Poh , et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh , et al., "Non-contact, automated cardiac pulse measurements using video imaging and blind source separation", OPT. Express 18, 2010, pp. 10762-10774, 14 pages.

Povsic, Klemen , et al., "Real-Time 3D visualization of the thoraco-abdominal surface during breathing with body movement and deformation extraction", Physiological Measurement, vol. 36, No. 7, May 28, 2015, pp. 1497-1516, 22 pages.

Prochazka , et al., "Microsoft Kinect Visual and Depth Sensors for Breathing and Heart Rate Analysis", Senors, vol. 16, No. 7, Jun. 28, 2016, 11 pages.

Rajan, V. , et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.

Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.

Reisner, A. , et al., "Utility of the Photoplethysmogram in Circulatory Monitoring", American Society of Anesthesiologist, May 2008, pp. 950-958, 9 pages.

Reyes, B.A. , et al., "Tidal vol. and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.

Rougier, Caroline , et al., "Robust Video Surveillance for Fall Detection Based on Human Shape Deformation", IEEE Transactions on Circuits and Systems for Video Technology, vol. 21, No. 5, May 2011, pp. 611-622, 12 pages.

Rubinstein, M , "Analysis and Visualization of Temporal Variations in Video", Department of Electrical Engineering and Computer Science, Massachusetts Institute of Technology, Feb. 2014, 118 pages.

Scalise, Lorenzo , et al., "Heart rate measurement in neonatal patients using a webcamera", Department of Industrial Engineering and Mathematical Science, Italy, 978-1-4673-0882-3/12, EEE, 2012, 4 pages.

Schaerer, J. , et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.

Sengupta, A. , et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.

Shah, Nitin , et al., "Performance of three new-generation pulse oximeters during motion and low perfursion in volunteers", Journal of Clinical Anesthesia, No. 24, 2012, pp. 385-391, 7 pages.

Shao, Dangdang , et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.

Shrivastava, H. , et al., "Classification with Imbalance: A Similarity-based Method for Predicting Respiratory Failure", IEEE International Conference on Bioinformatics and Biomedicine (IEEE BIBM2015), Washington, DC,USA, 2015, pp. 707-714, 8 pages.

Srinivas, J., et al., "A Mutual Authentication Framework for Wireless Medical Sensor Networks", Journal of Medical Systems, 41:80, 2017, pp. 1-19, 19 pages.

Sun, Yu , et al., "Motion-compensated noncontact imaging photoplethysmography to monitor cardiorespiratory status during exercise", Journal of Biomedical Optics, vol. 16, No. 7, Jul. 1, 2011, 10 pages.

Sun, Yu , et al., "Noncontact imaging photoplethysmography to effectively access pulse rate variability", Journal of Biomedical Optics, vol. 18(6), Jun. 2013, 10 pages.

Tamura , et al., "Wearable Photoplethysmographic Sensors-Past & Present", Electronics, vol. 3, 2014, pp. 282-302, 21 pages.

Tarassenko, L. , et al., "Non-contact video-based vital sign monitoring using ambient light and auto-regressive models", Institute of Physics and Engineering in Medicine, vol. 35, 2014, pp. 807-831, 26 pages.

Teichmann, D. , et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.

Transue, S. , et al., "Real-time Tidal vol. Estimation using Iso-surface Reconstruction", 2016 IEEE First International Conference on Connected Health: Applications, Systems and Engineering Technologies (CHASE), Jun. 27, 2016, pp. 209-218, 10 pages.

Verkruysee, Wim , et al., "Calibration of Contactless Pulse Oximetry", Anesthesia & Analgesia, vol. 124, No. 1, Jan. 2017, pp. 136-145, 10 pages.

Mllarroel, Mauricio , et al., "Continuous non-contact vital sign monitoring in neonatal intensive care unit", Healthcare Technology Letters, vol. 1, Issue 3, 2014, pp. 87-91, 5 pages.

Wadhwa, N. , et al., "Phase-Based Video Motion Processing", MIT Computer Science and Artificial Intelligence Lab, Jul. 2013, 9 pages.

Wadhwa, N. , et al., "Riesz pyramids for fast phase-based video magnification", In Proc. of IEEE International Conference on Computational Photography (ICCP), Santa Clara, CA, 2014, 10 pages.

Wang, W. , et al., "Exploiting spatial redundancy of image sensor for motion robust rPPG", IEEE Transactions on Biomedical Engineering, vol. 62, No. 2, 2015, pp. 415-425, 11 pages.

Wu, H.Y. , et al., "Eulerian video magnifcation for revealing subtle changes in the world", ACM Transactions on Graphics (TOG), vol. 31, No. 4, 2012, pp. 651-658, 8 pages.

Wulbrand, H. , et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Yu, M.C. , et al., "Noncontact Respiratory Measurement of Volume Change Using Depth Camera", 2012 Annual International Conference of the IEEE Engeineering in Medicine and Biology Society, Aug. 28, 2012, pp. 2371-2374, 4 pages.

Zaunseder , et al., "Spatio-temporal analysis of blood perfusion by imaging photoplethysmography", Progress in Biomedical Optics and Imaging, SPIE—International Society for Optical Engineering, vol. 10501, Feb. 20, 2018, 15 pages.

Zhou, J. , et al., "Maximum parsimony analysis of gene copy No. changes in tumor phylogenetics", 15th International Workshop on Algorithms in Bioinformatics WABI 2015, Atlanta, USA, 2015, pp. 108-120, 13 pages.

Rezaei, Mahdi , et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.

Sathyamoorthy, Adarsh Jagan, et al., "COVID-Robot: Monitoring Social Distancing Constraints in Crowded Scenarios", Aug. 21, 2020, pp. 1-11, 11 pages.

Liu, X., et al., "An Image Captioning Method for Infant Sleeping Environment Diagnosis", Springer International Publishing, May 15, 2019, pp. 18-26, 9 pages.

* cited by examiner

Airflow
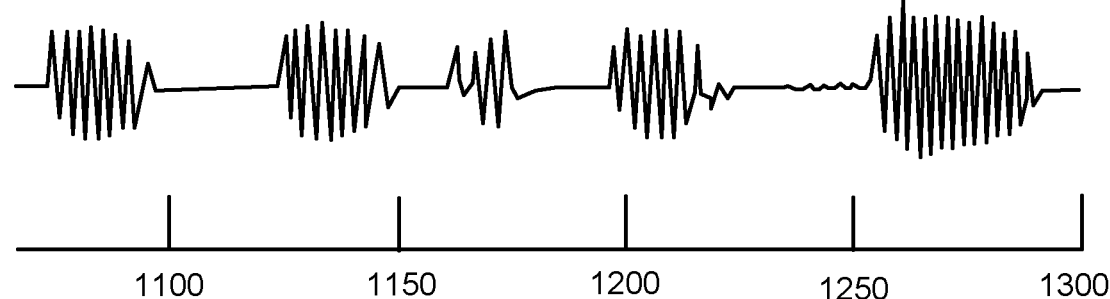
PPG
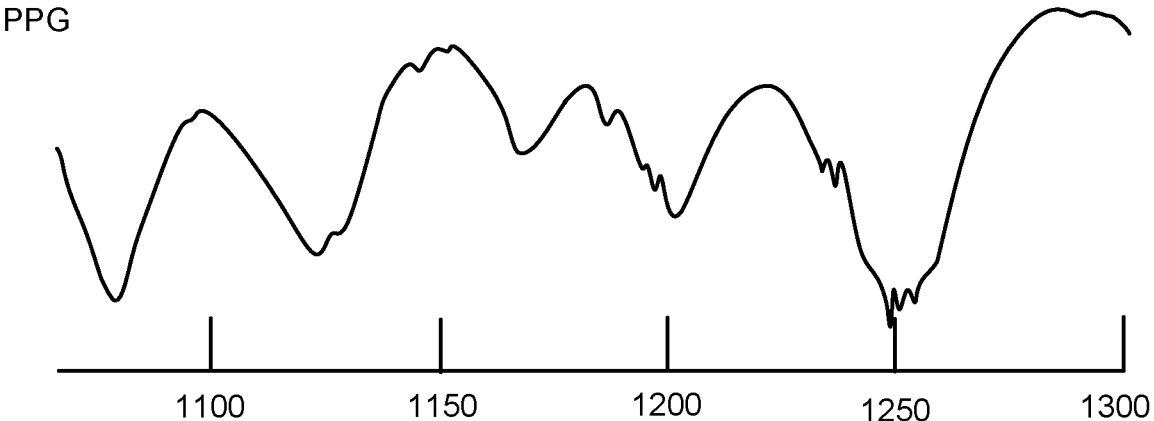
FIG. 11

MONITORING FOR SLEEP APNEA USING NON-CONTACT MONITORING SYSTEM AND PULSE OXIMETRY SYSTEM

CROSS-REFERENCE TO RELATED APPLICATION(S)

The present application claims benefit of priority to U.S. Provisional Patent Application No. 63/386,421, entitled "MONITORING FOR SLEEP APNEA USING NON-CON-TACT MONITORING SYSTEM AND PULSE OXIM-ETRY SYSTEM" and filed on Dec. 7, 2022, which is specifically incorporated by reference herein for all that it discloses or teaches.

BACKGROUND

There are several types of sleep apnea, but the most common is obstructive sleep apnea. This type of apnea occurs when the throat muscles intermittently relax and block the airway during sleep. A noticeable sign of obstructive sleep apnea is loud snoring. The snoring is usually loudest when sleeping on the back, and quiets when turned on the side. Other signs include episodes of stopped breathing during sleep, abrupt awakenings accompanied by gasping or choking, awakening with a dry mouth or sore throat, and morning headache.

Treatments for obstructive sleep apnea are available. One treatment involves using a device that uses positive pressure to keep the airway open while sleeping. Another option is a mouthpiece to thrust the lower jaw forward during sleep. In some cases, surgery might be an option.

Another type of sleep apnea is central sleep apnea. With central sleep apnea, the breathing repeatedly stops and starts during sleep. Central sleep apnea occurs because the brain does not send proper signals to the muscles that control your breathing. Central sleep apnea is different from obstructive sleep apnea, in which you can't breathe normally because of upper airway obstruction. Central sleep apnea is less common than obstructive sleep apnea.

Prior to determining which treatment option may be the best, a positive diagnosis of which sleep apnea is present needs to be made.

SUMMARY

The present disclosure is directed to using a system that includes non-contact patient monitoring system and a pulse oximetry system to monitor patients and detect symptoms that indicate the presence of sleep apnea, such as obstructive sleep apnea.

The methods of this disclosure utilize respiratory parameters (e.g., respiration rate, respiration volume) from the non-contact patient monitoring system to determine a reduction in or absence of the patient's respiration. The methods also utilize cardiological information (e.g., pulse) from a pulse oximetry system, which may be a contact or non-contact pulse oximeter sensor, to determine intrathoracic pressure increases from various modulations of the PPG signal during the patient's respiration cycle. An additional signal from a pulse oximeter that can optionally be used to verify the apnea event is the blood oxygen saturation (SpO2).

One particular embodiment described herein is a method for identifying sleep apnea that includes monitoring respiratory parameters of a patient with a non-contact monitoring system for a reduction in the monitored parameters; and monitoring a photoplethysmogram (PPG) parameter of the patient with a pulse oximetry system for a change in one or more of the amplitude modulation of the PPG parameter, the baseline modulation of the PPG parameter, and the frequency modulation of the PPG parameter. Upon realization of a reduction in the monitored respiratory parameters (e.g., a reduction by more than a threshold value), if an increase in one or more of the PPG parameters is detected, then an obstructive sleep apnea event is identified, and if no increase or a decrease in one or more of the PPG parameters is detected, then a central sleep apnea event is identified.

Another particular embodiment described herein is a method of detecting a sleep apnea event that includes monitoring respiratory parameters of a patient with a non-contact monitoring system for a reduction in the monitored parameters; and monitoring a photoplethysmogram (PPG) parameter of the patient with a pulse oximetry system. Dependent on detecting a reduction in the monitored respiratory parameters (e.g., a reduction by more than a threshold value) and a change in one or more of modulation of the amplitude of the PPG parameter, amplitude of a baseline modulation of the PPG parameter, and the amplitude of the change in frequency of the PPG parameter, then identifying the sleep apnea event. The event may be a central sleep apnea event or an obstructive sleep apnea event.

In either particular method, the reduction in a respiratory parameter by more than a threshold value could be, e.g., an amplitude reduction of at least 25%, at least 30% of 35%, at least 40%, at least 50%, at least 60%, at least 70%, at least 75%, at least 80%, or at least 90% compared to the previous amplitudes of the respiratory modulation values. An increase or reduction in one or more modulations of the PPG parameter could be, e.g., at least 20%, at least 25%, or at least 50% increase or decrease. An apnea event may be defined when the reduction lasts for at least 10 seconds, 15 seconds, 20 seconds, or 30 seconds.

Another particular embodiment described herein is a system for detecting and identifying sleep apnea, the system having a non-contact monitoring system for monitoring at least one respiration parameter of a patient, a pulse oximetry system for monitoring at least one PPG parameter, and a computer system programmed to process the data from the non-contact monitoring system and from the pulse oximetry system.

Other embodiments are also described and recited herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWING

FIG. 11 is a graphical representation of the airflow from a patient with obstructive sleep apnea and the corresponding PPG signal.

DETAILED DESCRIPTION

Figure 1:
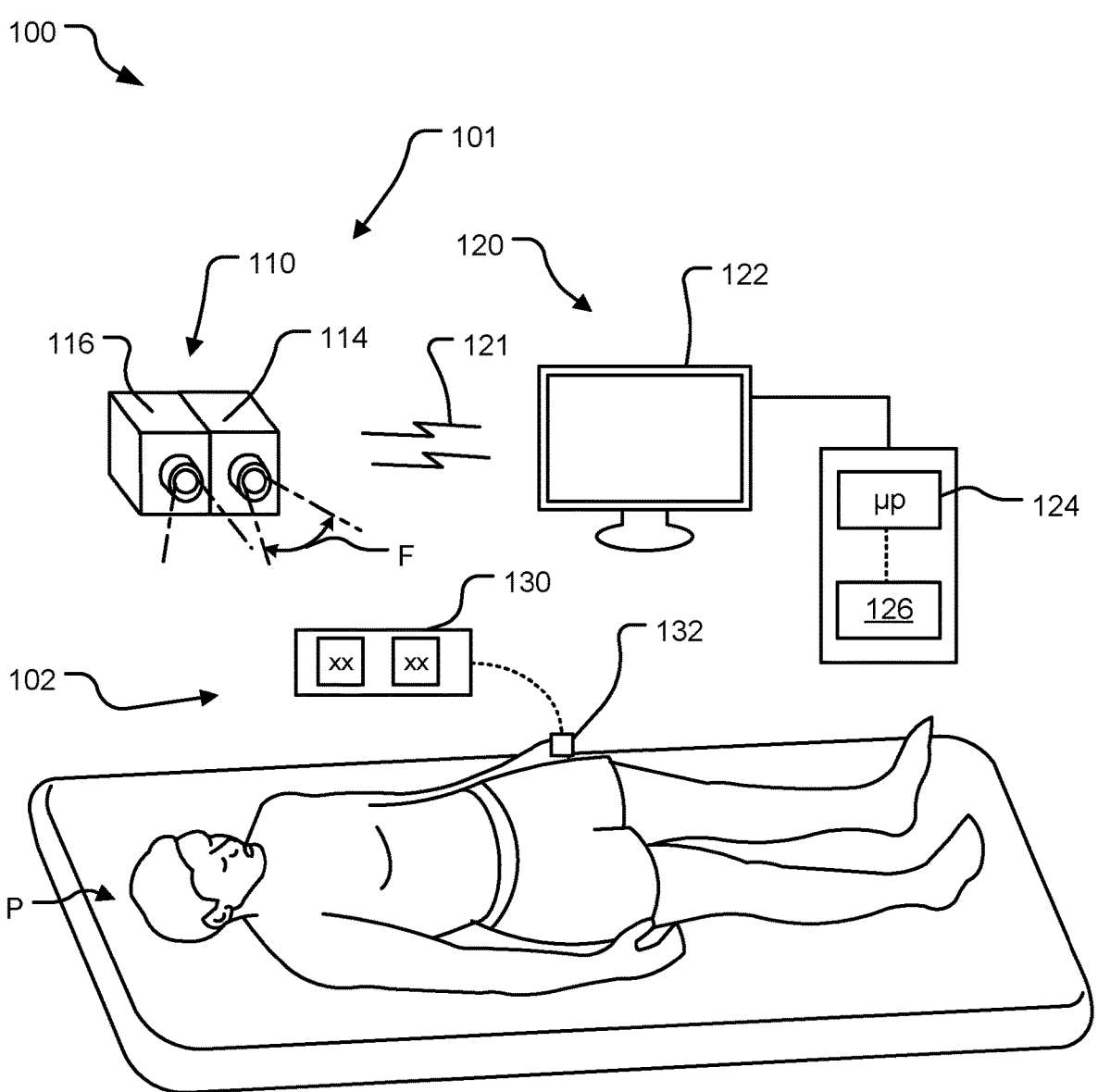
FIG. 1 is a schematic diagram of an example non-contact patient monitoring system with a contact pulse oximeter.

As described above, the present disclosure is directed to monitoring for symptoms related to obstructive sleep apnea events or episodes by using a contactless or non-contact patient monitoring system together with a pulse oximetry system.

The non-contact monitoring system can be used to monitor whether or not a particular symptom of obstructive sleep apnea occurs, particularly, a change in respiration activity such as respiration rate or depth (volume) of respiration. The pulse oximetry system can be used to monitor intrathoracic pressure, which can be corelated to increases in various modulations of the PPG signal during the breathing cycle. The monitoring may be done during daytime or nighttime, typically when the patient is sleeping.

The non-contact monitoring systems receive a video signal from the patient and from that extract a distance or depth signal from the relevant area to calculate the movement or motion from the depth signal. The systems can also receive a second signal, a light intensity signal reflected from the patient, and from that calculate the movement or motion from the light intensity signal. The movement or motion parameters from the two signals can be combined or compared to provide a qualified output parameter. In some embodiments, the light intensity signal is a reflection of an IR feature projected onto the patient, such as by a projector.

The depth sensing feature of the systems provides a measurement of the distance or depth between the detection system and the patient. One or two video cameras may be used to determine the depth, and change in depth, from the system to the patient. When two cameras, set at a fixed distance apart, are used, they offer stereo vision due to the slightly different perspectives of the scene from which distance information is extracted. When distinct features are present in the scene, the stereo image algorithm can find the locations of the same features in the two image streams. However, if an object is featureless (e.g., a smooth surface with a monochromatic color), then the depth camera system may have difficulty resolving the perspective differences. By including an image projector to project features (e.g., in the form of dots, pixels, etc.) onto the scene, this projected feature can be monitored over time to produce an estimate of changing distance or depth.

In the following description, reference is made to the accompanying drawing that forms a part hereof and in which is shown by way of illustration at least one specific embodiment. The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

FIG. 1 shows a patient monitoring system 100 and a subject or patient P being monitored. The system 100 includes a non-contact patient monitoring system 101 and a pulse oximetry monitoring system 102, which combine to monitor for symptoms of sleep apnea and to identify the type of sleep apnea encountered. The system 100 includes an appropriate computer system (having e.g., a processor, memory, software, etc.) configured to process the data from the non-contact patient monitoring system 101 and the pulse oximetry monitoring system 102.

The non-contact patient monitoring system 101 has a non-contact detector system 110 placed remote from the patient P. In this embodiment, the detector system 110 includes a camera system 114, particularly, a camera that includes an infrared (IR) detection feature. The camera 114 may be a depth sensing camera, such as a Kinect camera from Microsoft Corp. (Redmond, Washington) or a RealSense™ D415, D435 or D455 camera from Intel Corp. (Santa Clara, California). The camera system 114 is remote from the patient P, in that it is spaced apart from and does not physically contact the patient P. The camera system 114 may be, for example, mounted on a stand (e.g., a rollable stand) or affixed to a wall proximate the patient P, or to the bed of the patient P. The camera system 114 includes a detector exposed to a field of view F that encompasses at least a portion of the patient P.

The camera system 114 includes a depth sensing camera that can detect a distance between the camera system 114 and objects in its field of view F. Such information can be used to determine that a patient is within the field of view of the camera system 114 and determine a region of interest (ROI) to monitor on the patient. Once an ROI is identified, that ROI can be monitored over time, and the change in depth of points within the ROI can represent movements of the patient associated with, e.g., respiration.

The field of view F is selected based on the movement being monitored. For a patient where respiration rate and/or volume is being monitored, the chest of the patient is within the field of view. In some embodiments, the field of view F encompasses exposed skin of the patient. In other embodiments, the field of view F encompasses a monitored portion of the patient as covered by a blanket, sheet, or gown.

The camera system 114 operates at a frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 100 or 120 frames per second are helpful in avoiding aliasing with light flicker (for artificial lights having frequencies around 50 or 60 Hz).

The distance from the ROI on the patient P to the camera system 114 is measured by the system 101. Generally, the camera system 114 detects a distance between the camera system 114 and the surface within the ROI; the change in depth or distance of the ROI can represent movements of the patient, e.g., chest movement due to breathing.

In some embodiments, the system 101 determines a skeleton outline of the patient P to identify a point or points from which to extrapolate the ROI. For example, a skeleton may be used to find a center point of a chest, shoulder points, waist points, hands, feet or knees, and/or any other points on a body. These points can be used to determine the ROI. For example, the ROI may be defined by filling in the area around the knees. Certain determined points may define an outer edge of an ROI, such as shoulder points. In other embodiments, instead of using a skeleton, other points are used to establish an ROI. For example, a face may be recognized, and a torso and shoulder area inferred in proportion and spatial relation to the face. In other embodiments, the system 101 may establish the ROI around a point based on which parts are within a certain depth range of the point. In other words, once a point is determined that an ROI should be developed from, the system can utilize the depth information from the depth sensing camera system 114 to fill out the ROI as disclosed herein. For example, if a point on the chest is selected, depth information is utilized to determine the ROI area around the determined point that is a similar distance from the depth sensing camera 114 as the determined point. This area is likely to be a chest.

In another example, the patient P may wear a specially configured piece of clothing that identifies points on the body such as the legs or the hands. The system 101 may identify those points by identifying the indicating feature of the clothing. Such identifying features could be a visually encoded message (e.g., bar code, QR code, etc.), or a brightly colored shape that contrasts with the rest of the patient's clothing, etc. In some embodiments, a piece of clothing worn by the patient may have a grid or other identifiable pattern on it to aid in recognition of the patient and/or their movement. In some embodiments, the identifying feature may be stuck on the clothing using a fastening mechanism such as adhesive, a pin, etc., or stuck directly on the patient's skin, such as by adhesive. For example, a small sticker or other indicator may be placed on a patient's hands that can be easily identified from an image captured by a camera. In some embodiments, the indicator may be a sensor that can transmit a light or other information to the camera system 114 that enables its location to be identified in an image so as to help define the ROI. Therefore, different methods can be used to identify the patient and define an ROI.

The ROI size may differ according to the distance of the patient from the camera system. The ROI dimensions may vary linearly with the distance of the patient from the camera system. This ensures that the ROI scales according with the patient and covers the same part of the patient regardless of the patient's distance from the camera. This is accomplished by applying a scaling factor that is dependent on the distance of the patient (and the ROI) from the camera. In order to properly measure the depth changes, the actual size (area) of the ROI is determined and movements of that ROI are measured. The measured movements of the ROI and the actual size of the ROI are then used to calculate a respiratory parameter, e.g., a respiratory rate or volume. Because a patient's distance from a camera can change, e.g., due to rolling or position readjustment, the ROI associated with that patient can appear to change in size in an image from a camera. However, using the depth sensing information captured by a depth sensing camera or other type of depth sensor, the system can determine how far away from the camera the patient (and their ROI) actually is. With this information, the actual size of the ROI can be determined, allowing for accurate measurements of depth change regardless of the distance of the camera to the patient.

In some embodiments, the system 101 may receive a user input to identify a starting point for defining an ROI. For example, an image may be reproduced on an interface, allowing a user of the interface to select a point on the patient from which the ROI can be determined (such as a point on the chest or legs). Other methods for identifying a patient, points on the patient, and defining an ROI, may also be used.

However, if the ROI is essentially featureless (e.g., a smooth surface with a monochromatic color, such as a blanket or sheet covering the patient P), then the camera system 114 may have difficulty resolving the perspective differences. To address this, the system 101 includes a projector 116 to project individual features (e.g., dots, crosses or Xs, lines, individual pixels, etc.) onto the ROI; the features may be visible light, UV light, infrared (IR) light, etc. The projector may be part of the detector system 110 or the overall non-contact system 101.

The projector 116 generates a sequence of features over time on the ROI from which is monitored and measured the reflected light intensity. A measure of the amount, color, or brightness of light within all or a portion of the reflected feature over time is referred to as a light intensity signal. The camera system 114 detects the features from which this light intensity signal is determined. In an embodiment, each visible image projected by the projector 116 includes a two-dimensional array or grid of pixels, and each pixel may include three color components—for example, red, green, and blue. A measure of one or more color components of one or more pixels over time is referred to as a "pixel signal," which is a type of light intensity signal. In another embodiment, when the projector 116 projects an IR feature, which is not visible to a human eye, the camera system 114 includes an infrared (IR) sensing feature. In another embodiment, the projector 116 projects a UV feature. In yet other embodiments, other modalities including millimeter-wave, hyper-spectral, etc., may be used.

The projector 116 may alternately or additionally project a featureless intensity pattern (e.g., a homogeneous pattern, a gradient or any other pattern that does not necessarily have distinct features). In some embodiments, the projector 116, or more than one projector, can project a combination of feature-rich and featureless patterns on to the ROI.

The light intensity of the image reflected by the patient surface is detected by the detector system 110.

The detected images and/or diffusion measurements are sent to a computing device 120 through a wired or wireless connection 121. The computing device 120 includes a display 122, a processor 124, and hardware memory 126 for storing software and computer instructions. Sequential image frames of the patient P are recorded by the video camera system 114 and sent to the computing device 120 for analysis by the processor 124. The display 122 may be remote from the computing device 120, such as a video screen positioned separately from the processor and memory. Other embodiments of the computing device 120 may have different, fewer, or additional components than shown in FIG. 1. In some embodiments, the computing device may be a server. In other embodiments, the computing device of FIG. 1 may be connected to a server. The captured images (e.g., still images or video) can be processed or analyzed at the computing device and/or at the server to determine the motion of the patient P as disclosed herein.

The non-contact monitoring system 101, as described herein and variations thereof, can determine respiration parameters, e.g., respiration rate and respiration volume, which are useful in identifying sleep apnea, such as obstructive sleep apnea.

The system 100 also includes the pulse oximetry monitoring system 102. A conventional, contact, pulse oximetry, utilizes a sensor having two light emitters and a photodetector. The sensor is placed in contact with the patient, such as by clipping or adhering the sensor around a finger, toe, or ear of the patient. The sensor's emitters emit light of two particular wavelengths into the patient's tissue, and the photodetector detects the light after it is reflected or transmitted through the tissue. The detected light signal, called a photoplethysmogram (PPG), modulates with the patient's heartbeat, as each arterial pulse passes through the monitored tissue and affects the amount of light absorbed or scattered.

During an obstructive sleep apnea event, the intrathoracic pressure increases, which causes increases in various modulations of the PPG signal during the breathing cycle. This includes increases in the modulation of the amplitude of the PPG pulse, the amplitude of the baseline modulation of the PPG signal, and the amplitude of the change in frequency of the PPG over the breathing signal (the latter being commonly known clinically as respiratory sinus arrythmia (RSA)).

In FIG. 1, the pulse oximetry monitoring system 102 includes an oximeter 130 operably connected to a sensor 132, shown as in contact with the patient's finger. The sensor 132 may be wired or wirelessly connected (e.g., via Bluetooth connectivity, Wi-Fi connectivity, infrared, visible light, radio frequency (RF) signals, or other wireless protocols/methods) to the oximeter 130.

In other embodiments, the pulse oximetry monitoring system 102 may be a non-contact pulse oximetry system.

Figure 2:
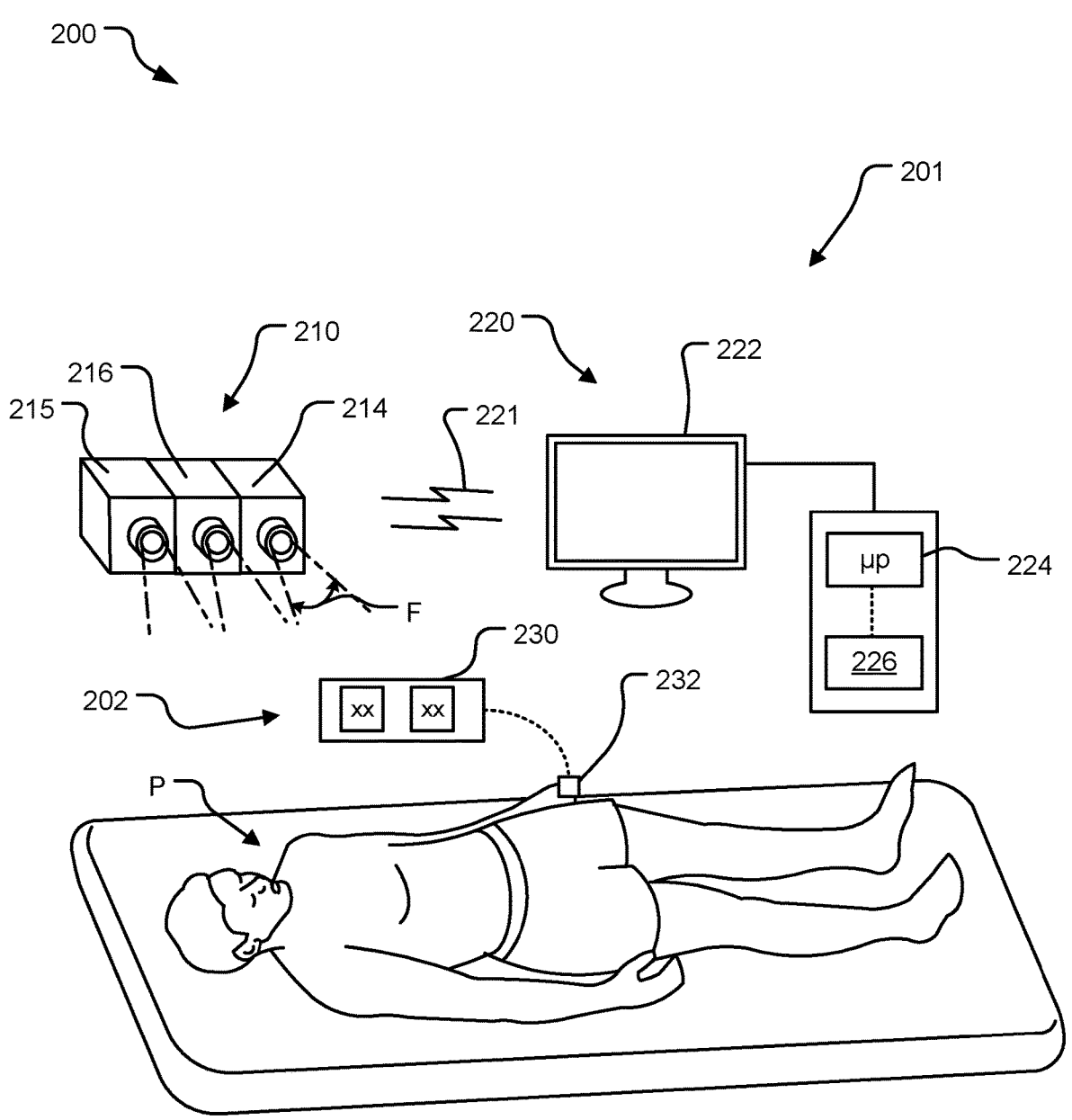
FIG. 2 is a schematic diagram of another example non-contact patient monitoring system with a contact pulse oximeter.

FIG. 2 shows another patient monitoring system 200 and a patient P. The system 200 includes a non-contact patient monitoring system 201 having a non-contact detector 210 placed remote from the patient P and a pulse oximetry monitoring system 202, in this embodiment, a portion of which is in contact with the patient P. The system 200 includes an appropriate computer system (having e.g., a processor, memory, software, etc.) configured to process the data from the non-contact patient monitoring system 201 and the pulse oximetry monitoring system 202.

In this embodiment, the detector 210 includes a first camera 214 and a second camera 215, at least one of which includes an infrared (IR) camera feature. The cameras 214, 215 are positioned so that their ROIs at least intersect, in some embodiments, completely overlap. The detector 210 also includes an IR projector 216, which projects individual features (e.g., dots, crosses or Xs, lines, or a featureless pattern, or a combination thereof etc.) onto the ROI. The projector 216 can be separate from the detector 210 or integral with the detector 210, as shown in FIG. 2. In some embodiments, more than one projector 216 can be used. Both cameras 214, 215 are aimed to have features projected by the projector 216 to be in their ROI. The cameras 214, 215 and projector 216 are remote from the patient P, in that they are spaced apart from and do not contact the patient P. In this implementation, the projector 216 is physically positioned between the cameras 214, 215, whereas in other embodiments it may not be so.

The distance from the ROI to the cameras 214, 215 is measured by the system 200. Generally, the cameras 214, 215 detect a distance between the cameras 214, 215 and the projected features on a surface within the ROI. The light from the projector 216 hitting the surface is scattered/diffused in all directions; the diffusion pattern depends on the reflective and scattering properties of the surface. The cameras 214, 215 also detect the light intensity of the projected individual features in their ROIs. From the distance and the light intensity, movement of the patient P is monitored.

As with the pulse oximetry monitoring system 102 of the system 100 of FIG. 1, the pulse oximetry monitoring system 202 includes an oximeter 230 operably connected to a sensor 232, shown as in contact with the patient's finger. The sensor 232 may be wired or wirelessly connected (e.g., via Bluetooth connectivity, Wi-Fi connectivity, infrared, visible light, radio frequency (RF) signals, or other wireless protocols/methods) to the oximeter 230.

Figure 3:
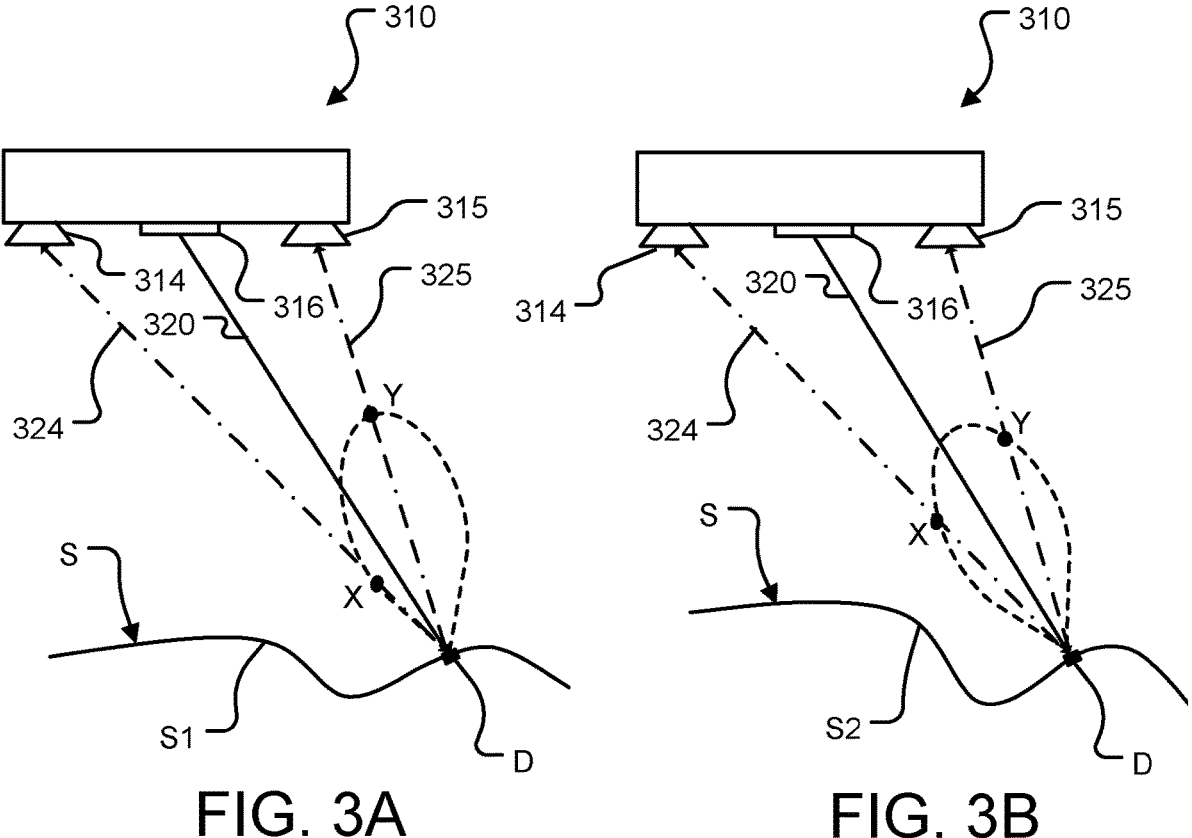
FIGS. 3A and 3B are schematic diagrams showing two embodiments using the example non-contact patient monitoring system of FIG. 2.

FIG. 3A and FIG. 3B both show a non-contact detector 310 having a first camera including an IR detection feature 314, a second IR camera including an IR detection feature 315, and an IR projector 316. A dot D is projected by the projector 316 onto a surface S, e.g., of a patient, via a beam 320. Light from the dot D is reflected by the surface S and is detected by the camera 314 as beam 324 and by the camera 315 as beam 325.

The light intensity returned to and observed by the cameras 314, 315 depends on the diffusion pattern caused by the surface S (e.g., the surface of a patient), the distance between the cameras 314, 315 and the surface S, the surface gradient, and the orientation of the cameras 314, 315 relative to the surface S. In FIG. 3A, the surface S has a first profile S1 and in FIG. 3B, the surface S has a second profile S2 different than S1; as an example, the first profile S1 is with the patient in a first position and the second profile S2 is with the patient in a second position. Because the surface profiles S1 and S2 differ, the deflection pattern from the dot D on each of the surfaces differs.

During movement of the patient, e.g., movement of the patient's chest during respiration, the light intensity reflection off the dot D observed by the cameras 314, 315 changes because the surface profile S1 and S2 (specifically, the gradient) changes as well as the distance between the surface S and the cameras 314, 315. FIG. 3A shows the surface S having the surface profile S1 at time instant $t=t_n$ and FIG. 3B shows the surface S having the surface profile S2 at a later time, specifically $t=t_{n+1}$, with S2 being slightly changed due to movement. Consequently, the intensity of the projected dot D observed by the cameras 314, 315 will change due to the changes of the surface S. In FIG. 3A, a significantly greater intensity is measured by the camera 315 than by the camera 314, seen by the x and y on the beams 324, 325, respectively. In FIG. 3B, y is less than y in FIG. 3A, whereas x in FIG. 3B is greater than x in FIG. 3A. The manner in how these intensities change depends on the diffusion pattern and its change over time. As seen in FIGS. 3A and 3B, the light intensities as measured by the cameras 314, 315 have changed between FIGS. 3A and 3B, and hence, the surface S has moved. Each camera generates a signal because of the change of the intensity of dot D when the surface profile changes from time instant $t=t_n$ to $t=t_{n+1}$ due to movement.

In some other embodiments, a single camera and light projector can be used. For example, in FIGS. 3A and 3B, the camera 315 is not present or is ignored; the camera 314 will still produce a change in light intensity from time instant $t=t_n$ to $t=t_{n+1}$ due to movement. Such an embodiment will therefore produce only a single signal as opposed to the two signals generated by the embodiment discussed in the previous paragraph.

Figure 4:
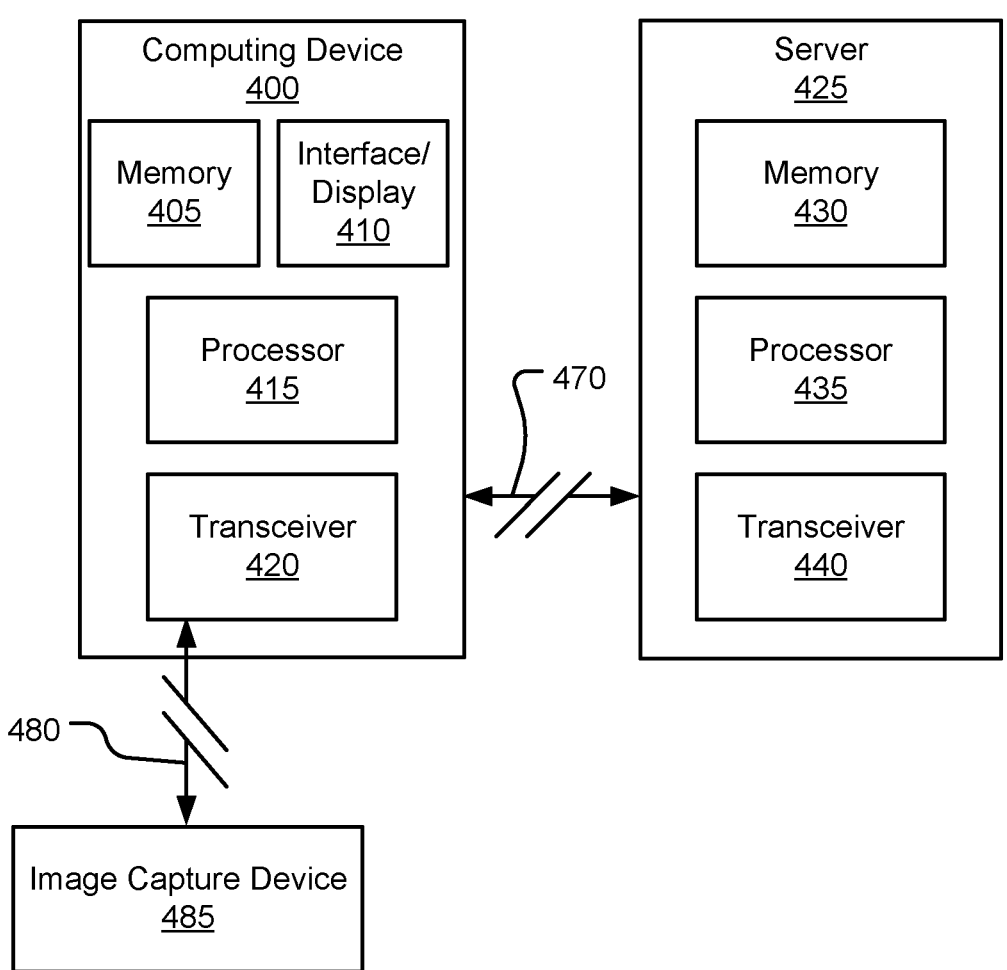
FIG. 4 is a block diagram of a computing device, a server, and an image capture device of a non-contact patient monitoring system.

FIG. 4 is a block diagram illustrating a non-contact monitoring system, such as the non-contact monitoring system 101 or the non-contact monitoring system 201, including a computing device 400, a server 425, and an image capture device 485 (e.g., a camera, e.g., the camera system 114 or cameras 214, 215). In various embodiments, fewer, additional and/or different components may be used in the system.

The computing device 400 includes a processor 415 that is coupled to a memory 405. The processor 415 can store and recall data and applications in the memory 405, including applications that process information and send commands/signals according to any of the methods disclosed herein. The processor 415 may also display objects, applications, data, etc. on an interface/display 410. The processor 415 may also or alternately receive inputs through the interface/display 410. The processor 415 is also coupled to a transceiver 420. With this configuration, the processor 415, and subsequently the computing device 400, can communicate with other devices, such as the server 425 through a connection 470 and the image capture device 485 through a connection 480. For example, the computing device 400 may send to the server 425 information determined about a patient from images captured by the image capture device 485, such as depth information of a patient in an image.

The server 425 also includes a processor 435 that is coupled to a memory 430 and to a transceiver 440. The processor 435 can store and recall data and applications in the memory 430. With this configuration, the processor 435, and subsequently the server 425, can communicate with other devices, such as the computing device 400 through the connection 470.

The computing device 400 may be, e.g., the computing device 120 of FIG. 1 or the computing device 220 of FIG. 2. Accordingly, the computing device 400 may be located remotely from the image capture device 485, or it may be local and close to the image capture device 485 (e.g., in the same room). The processor 415 of the computing device 400 may perform any or all of the various steps disclosed herein. In other embodiments, the steps may be performed on a processor 435 of the server 425. In some embodiments, the various steps and methods disclosed herein may be performed by both of the processors 415 and 435. In some embodiments, certain steps may be performed by the processor 415 while others are performed by the processor 435. In some embodiments, information determined by the processor 415 may be sent to the server 425 for storage and/or further processing.

The devices shown in the illustrative embodiment may be utilized in various ways. For example, either or both of the connections 470, 480 may be varied. For example, either or both the connections 470, 480 may be a hard-wired connection. A hard-wired connection may involve connecting the devices through a USB (universal serial bus) port, serial port, parallel port, or other type of wired connection to facilitate the transfer of data and information between a processor of a device and a second processor of a second device. In another example, one or both of the connections 470, 480 may be a dock where one device may plug into another device. As another example, one or both of the connections 470, 480 may be a wireless connection. These connections may be any sort of wireless connection, including, but not limited to, Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In yet another example, the various devices may connect through an internet (or other network) connection. That is, one or both of the connections 470, 480 may represent several different computing devices and network components that allow the various devices to communicate through the internet, either through a hard-wired or wireless connection. One or both of the connections 470, 480 may also be a combination of several modes of connection.

The configuration of the devices in FIG. 4 is merely one physical system in which the non-contact monitoring system may be executed. Other configurations of the devices shown may exist to practice the disclosed embodiments. It will be appreciated that many various combinations of computing devices may execute the methods and systems disclosed herein. Examples of such computing devices may include other types of medical devices and sensors, infrared cameras/detectors, night vision cameras/detectors, other types of cameras, radio frequency transmitters/receivers, smart phones, personal computers, servers, laptop computers, tablets, RFID enabled devices, or any combinations of such devices.

The method of this disclosure utilizes depth (distance) information between the camera(s) and the patient to determine movement, e.g., repeated movement indicative of respiration. A depth image or depth map, which includes information about the distance from the camera to each point in the image, can be measured or otherwise captured by a depth sensing camera, such as a Kinect camera from Microsoft Corp. (Redmond, Washington) or a RealSense™ D415, D435 or D455 camera from Intel Corp. (Santa Clara, California) or other sensor devices based upon, for example, millimeter wave and acoustic principles to measure distance.

The depth image or map can be obtained by a stereo camera, a camera cluster, camera array, or a motion sensor focused on a ROI, such as a patient's hands or legs. In some embodiments, the camera(s) are focused on visible or IR features in the ROI. Each projected feature may be monitored, less than all the features in the ROI may be monitored or all the pixels in the ROI can be monitored.

When multiple depth images are taken over time in a video stream, the video information includes the movement of the points within the image, as they move toward and away from the camera over time.

Because the image or map includes depth data from the depth sensing camera, information on the spatial location of the patient (e.g., the patient's legs) in the ROI can be determined. This information can be contained, e.g., within a matrix. For example, as the patient's chest or torso moves, it changes the depth information associated with the images over time. As a result, the location information associated with the ROI changes over time.

As indicated above, in addition to the methodology of this disclosure utilizing depth (distance) information between the camera(s) and the patient to determine movement of the patient, the method can also use reflected light intensity from projected IR features (e.g., dots, grid, stripes, crosses, squares, etc., or a featureless pattern, or a combination thereof) in the scene to estimate the depth (distance).

This change of intensity of each of the projected features is used to indicate movement of the surface on which the feature was projected. The intensity signal is formed by aggregating all the pixel values, at an instant in time, from across the ROI to generate a pattern signal. In some embodiments, less than all the projected features in the ROI are monitored; for example, only a random sampling of the projected features is monitored, or for example, every third feature is monitored. In some embodiments, each feature reflection is monitored only for a predetermined duration, to determine which projected features provide an accurate or otherwise desired light intensity signal, and then those selected features are monitored to obtain the signal. In some embodiments, each pixel in the ROI is monitored and the light intensity signal obtained.

This method for producing a movement signal, i.e., from the intensity of the light diffusion, is independent from the depth data used to produce a signal representative of the movement. This secondary pattern signal, from the light intensity, can be used to enhance or confirm the measurement from the depth data. The movement indicated by the varying reflected intensity, typically closely matches the movement determined by the depth (distance) measured by the depth camera(s), e.g., camera system 114, cameras 214, 215.

Returning to and with respect to FIG. 2 and FIGS. 3A and 3B above, it is described that the system 200 with two cameras 214, 215 or the system with two cameras 314, 315 can be used, the two cameras 214, 215 and 314, 315 providing a stereo property for one or both of the depth signal and the light intensity signal. When two cameras are used, although both cameras will produce very similar results, they each have their own noise characteristics. The noise, which is added to the movement signal, is generally uncorrelated and the overall noise component is therefore reduced by combining the results of two cameras. Thus, each camera produces a movement pattern and the results may then be, for example, averaged. Note that more than two cameras may be used to further improve the performance. Additionally, e.g., other, more advanced, methods for combining/fusing the different signals may be used including Kalman and particle filtering.

Thus, described herein are methods and systems for non-contact monitoring of a patient to determine movement by utilizing a distance or depth signal from the patient to the system and by utilizing a reflected light intensity signal from projected IR features to derive the same parameter(s). The parameter(s) from the two signals are combined or compared to provide an output parameter value or signal.

The method of this disclosure also utilizes cardiological information (e.g., pulse) from a pulse oximetry system, which may be a contact or non-contact pulse oximeter sensor, to determine intrathoracic pressure increases from various modulations of the PPG signal during the breathing cycle.

Figure 5:
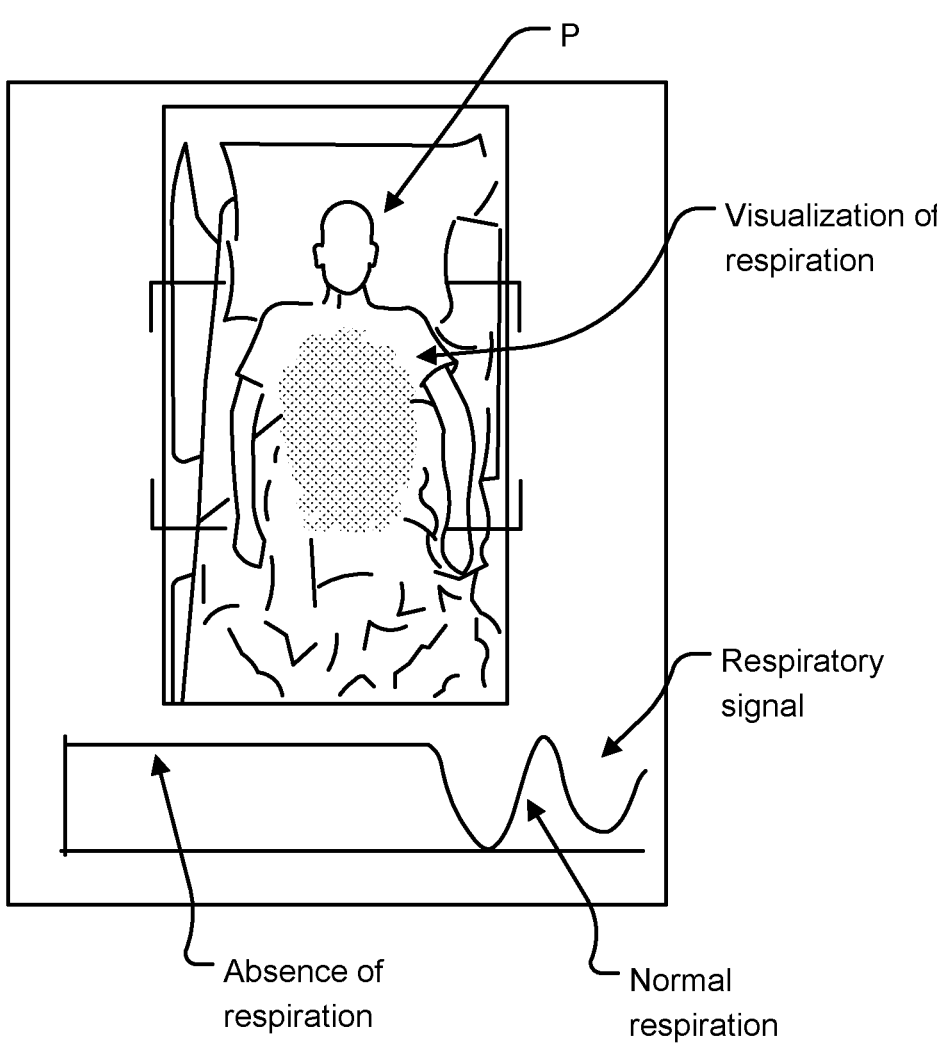
FIG. 5 is a schematic representation of an output image from a non-contact monitoring system.

FIG. 5 shows an output image from a non-contact monitoring system, such as the non-contact monitoring system 101 or the non-contact monitoring system 201, having a depth-sensed scene that includes the patient P with a visualization of breathing superimposed over the torso of the patient. Also shown in FIG. 5 is a graphical representation of the respiratory signal (rate) determined from the changes in depth across the scene. The respiratory signal shows a duration of an absence of respiration, indicative of a possible apnea event, and a duration of normal respiration.

Figure 6:
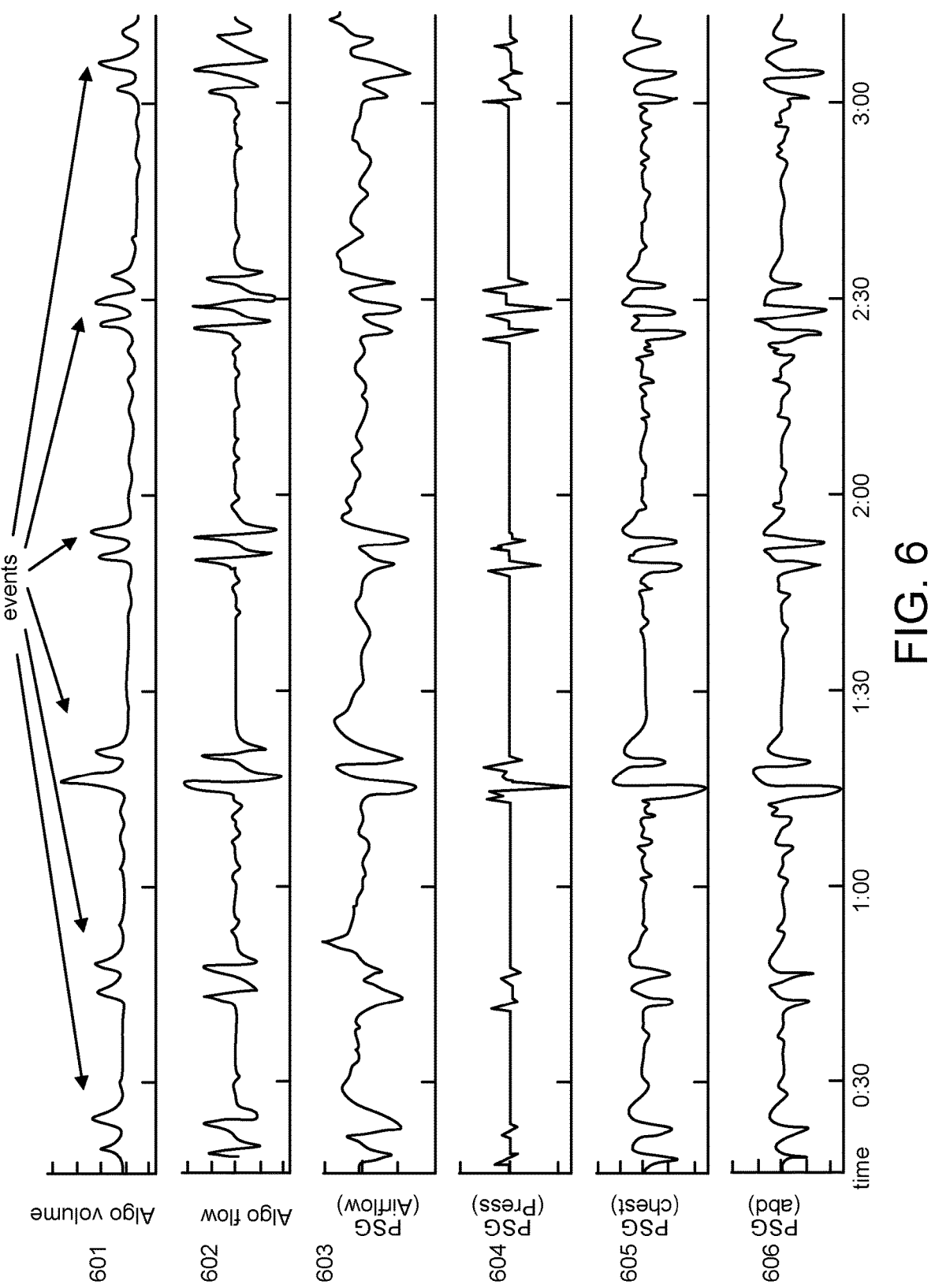
FIG. 6 shows graphical representations of various respiratory parameters.

A non-contact patient monitoring system, such as the non-contact patient monitoring system 101 or the non-contact patient monitoring system 201, can be very good at identifying respiration events, e.g., in sleep studies. FIG. 6 provides numerous graphical outputs representing respiration events from sleep studies, identified as graphs 601, 602, 603, 604, 605, and 606.

In FIG. 6, where the top two graphs 601 and 602 are the volume signal and the flow signal, respectively, obtained from an example non-contact patient monitoring system during a sleep study. The bottom four graphs 603, 604, 605, 606 are from the simultaneously collected PSG signals: airflow signal (603), pressure signal (604), chest band signal (605) and abdominal band signal (606). The match in finding the same events in all signals is evident from the aligned graphs.

Figure 7:
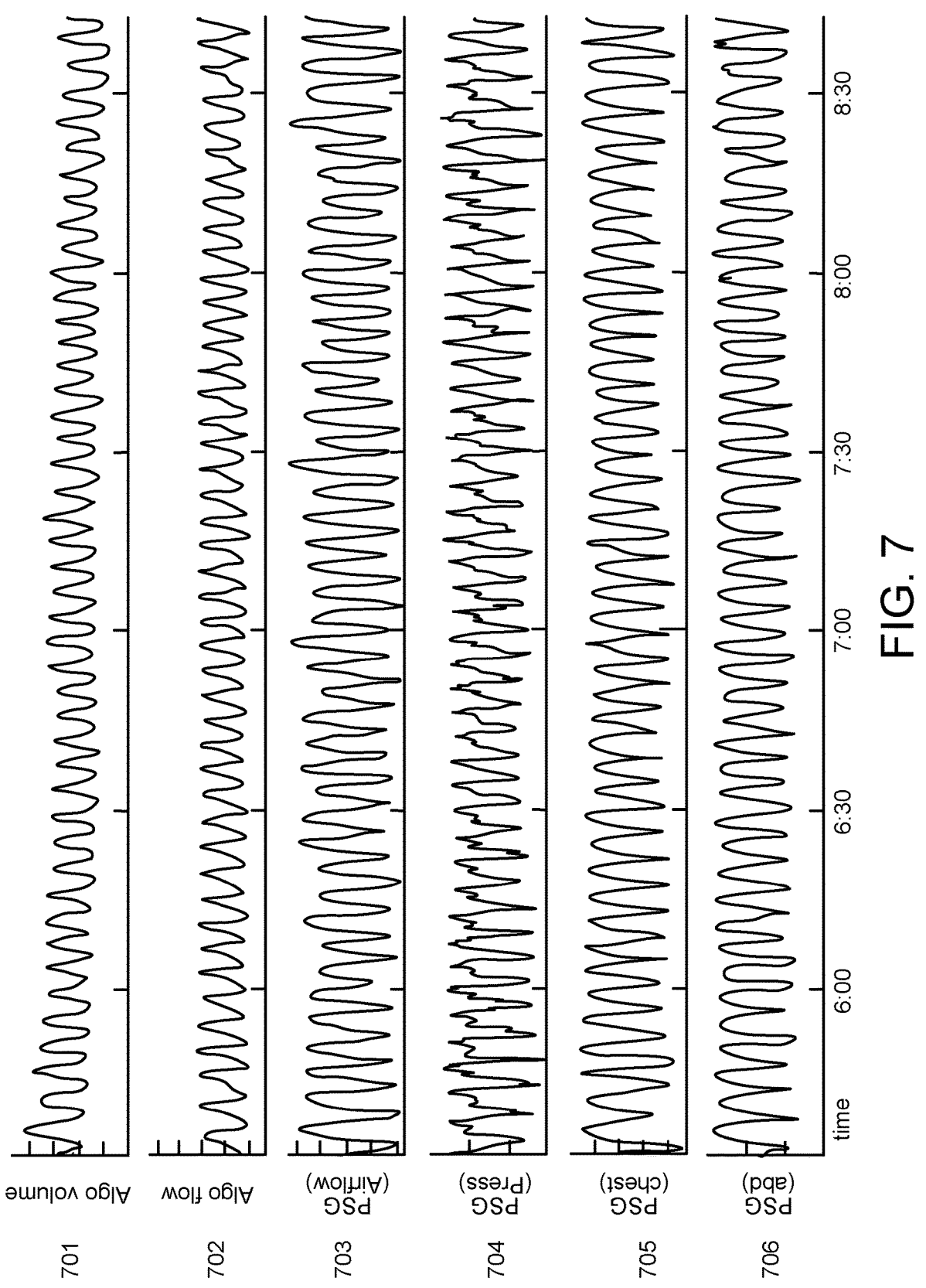
FIG. 7 shows additional graphical representations of the various respiratory parameters.

FIG. 7 contains another set of subplots of the signals collected during a more regular breathing phase in the same study, this time at the beginning of the sleep study. Shown in FIG. 7 are the volume signal (701) and the flow signal (702) obtained from the non-contact patient monitoring system and the simultaneously collected PSG signals: airflow signal (703), pressure signal (704), chest band signal (705) and abdominal band signal (706). Again, the match in finding the same events in all signals is evident from the aligned graphs.

Figures 8A, 8B, 8C, 8D:
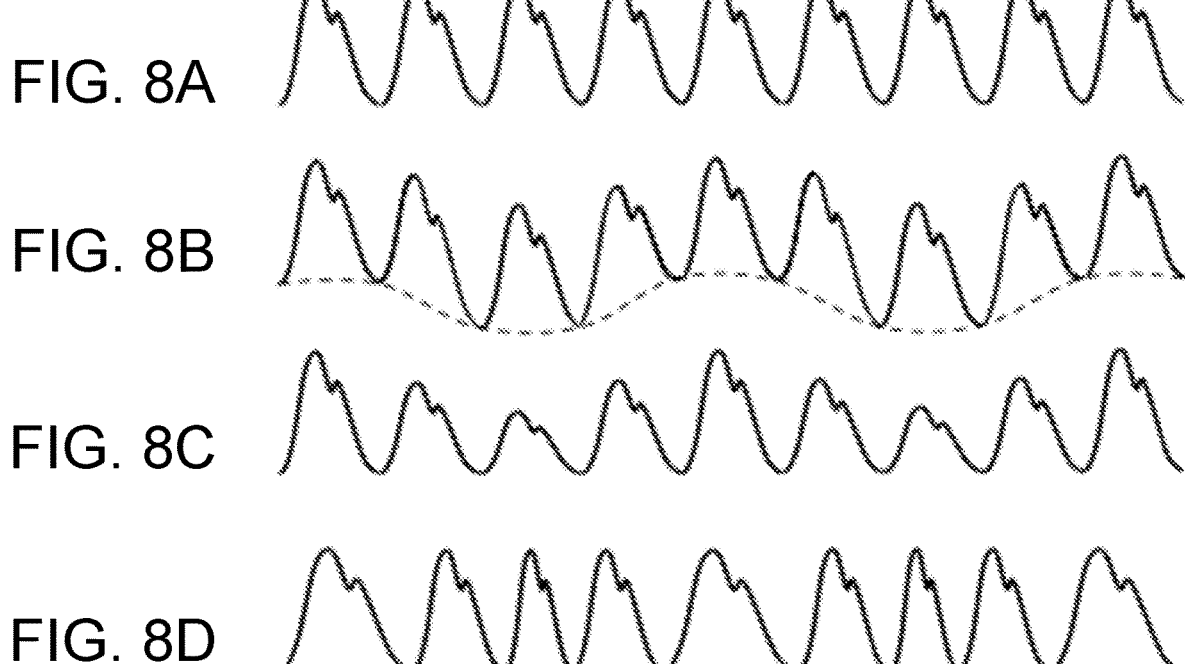
FIGS. 8A, 8B, 8C and 8D are graphical representations of PPG modulations.

As indicated above, in an obstructive sleep apnea event, the intrathoracic pressure increases, which causes increases in various modulations of the PPG signal during the breathing cycle. These increases include, and can be, in the amplitude modulation of the PPG pulse, the baseline modulation of the PPG signal and the frequency modulation of the PPG. Examples of these modulations are shown in FIG. 8B (the modulation of the amplitude of the PPG pulse), FIG. 8C (the modulation of the baseline of the PPG signal) and FIG. 8D (the modulation in the frequency of the PPG over the breathing signal) and can be compared to a PPG with no respiratory modulations, shown in FIG. 8A.

Figure 9:
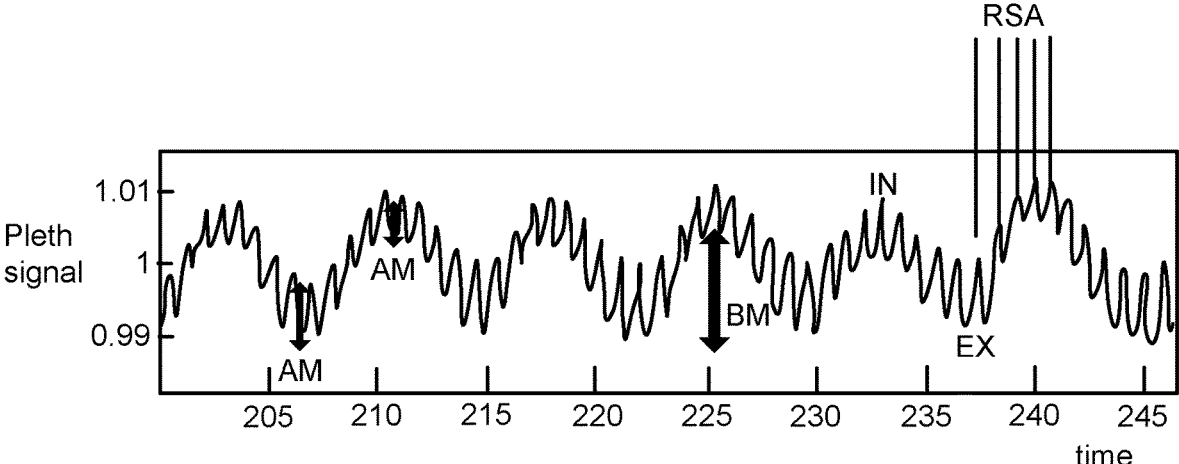
FIG. 9 is a graphical representation of a PPG over a six-breath cycle.

FIG. 9 shows a PPG signal collected over a six-breath cycle, where the respiratory modulations are evident in the signal: amplitude modulation (AM), baseline modulation (BM), respiratory sinus arrythmia (RSA).

In one example method, the respiratory waveform is tracked over time for the detection of a clear reduction in, or absence of, respiratory waveforms in the signal from the non-contact patient monitoring system (e.g., the non-contact monitoring system 101 or the non-contact monitoring system 201). The PPG respiratory modulation from the pulse oximetry system (e.g., the pulse oximetry system 102 or the pulse oximetry system 202) is checked to determine whether an obstructive or central event has occurred. If, during the absence or reduction of a respiratory waveform in the touchless signal, an increase in the amplitude of one or more PPG respiratory modulations is observed, it may be determined that an obstructive event is taking place. If, during the absence or reduction of a respiratory waveform in the touchless signal, a decrease in the amplitude of one or more PPG respiratory modulations is observed, it may be determined that a central event is taking place.

Figure 10:
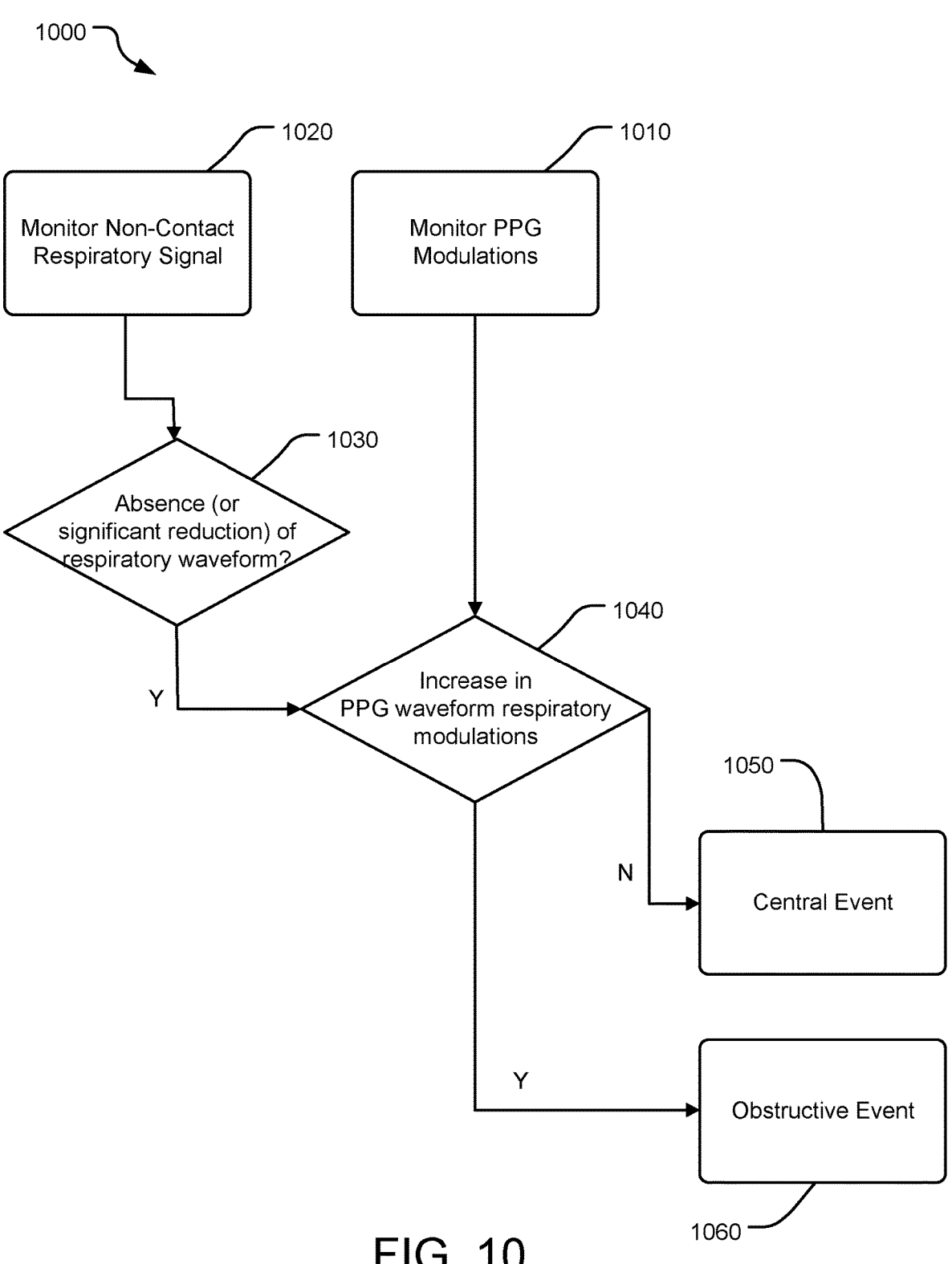
FIG. 10 is a flow chart of a stepwise method for determining an apnea event.

FIG. 10 shows, stepwise, an overall example method 1000 for determining the occurrence of a sleep apnea event, either a central event or an obstructive event. In a first step 1010, PPG modulations are monitored with a pulse oximetry system. Simultaneously, subsequently, or before the step 1010, the respiratory signal from a non-contact patient monitoring system is monitored in step 1020. When, in step 1030, an absence of, or reduction of, the respiratory waveform is detected, the results from the step 1010 are reviewed in step 1040 to determine if an increase in PPG waveform that corresponds to respiratory modulations was observed. If "no," the event is a central event in step 1050, but if "yes," the event is defined as an obstructive event in step 1060. In some embodiments, the reduction of the respiratory waveform must be a reduction that is greater than a first threshold value.

In either instance, whether the apnea event is a central event or an obstructive event, an alarm (e.g., audible) may be triggered by the system, to awaken the patient.

As indicated above, in step 1030 an absence of or reduction (in some embodiments, a reduction greater than a threshold value) of the waveform amplitude, compared to a previous, steady-state amplitude, is detected in order to determine if an apnea state is present. The threshold value of the reduction could be, e.g., an amplitude reduction of at least 25%, at least 30%, at least 35%, at least 40%, at least 50%, at least 60%, at least 70%, at least 75%, at least 80%, or at least 90% compared to the previous amplitudes of the respiratory modulation values. These amplitude values could be the peak value or a mean or average value of the respiration prior to the event. Complete absence of the respiratory signal would be a 100% reduction in respiration.

With respect to the increase or reduction in one or more modulations of the PPG parameter, the increase or decrease must be more than a threshold value. The threshold value for the PPG parameter may be the same as or different from the threshold value for the respiratory waveform. In some embodiments, the threshold values are different, and the threshold value for the respiratory waveform is identified as a first threshold value, while the threshold value for the PPG parameter is identified as a second threshold value. As indicated above, in step 1040 the second threshold value for an increase or reduction in one or more modulations of the PPG parameter (e.g., AM, BM, RSA) could be, e.g., at least 20%, at least 25%, or at least 50% increase or decrease over a breath cycle.

An apnea may be defined when the reduction lasts for at least 10 seconds, 15 seconds, 20 seconds, 30 seconds, etc.

Examples of reductions that would qualify as a reduction greater than a threshold value (for any one or more of the respiratory modulation values) include, e.g., a reduction of at least 25% for 45 seconds, a reduction of at least 50% for at 30 seconds, at least 75% reduction for at least 20 seconds, at least 90% reduction for at least 15 seconds. A complete absence of respiration for, e.g., at least 10 seconds, can quality for an apnea event.

Whether the method 1000, a variant thereof, or any other method using a system such as the system 100 or the system 200 described herein, one or more thresholds may be included in the method so that only when the increase or decrease in the amplitude of the resulting respiratory modulations are above or below a threshold is the type of event identified.

Any additional logic may be included in the method whereby if one or more of the three modulations (e.g., amplitude modulation (AM), baseline modulation (BM), respiratory sinus arrythmia (RSA)) increase or decrease above certain thresholds then it is determined that an event has been detected. Example thresholds would be a decrease of at least 50%, or 70%, 75%, or 80% or even more than 90%, than previous values to indicate a central apnea event. Thresholds to indicate an obstructive apnea event include, e.g., at least 20% or 25%, 50%, 70%, 75%, or 80%, or even 100%. Threshold durations could be similar to actual measurements, e.g., at least 10 seconds, 15 seconds, 20 seconds, 30 seconds, etc., to see the drop or increase. Any of the thresholds may be derived from historical data sets. Alternatively, they may be derived from the modulations of that patient during regular breathing prior to the apneic event.

Instead of using explicit thresholds, a machine learning model may be trained on the PPG data or on measures derived from the PPG signal (e.g., the pulse amplitude, recent baseline changes, etc.). A more accurate determination of obstructive apnea may be possible with a machine learning model. Suitable machine learning models may be a neural network, a decision tree, a random forest, a support vector machine or other suitable machine learning model.

The above example assumes that the paradoxical breathing on the torso of the patient during obstructive apnea cancels out the depth information used to determine the respiratory signal from the non-contact patient monitoring touchless system (i.e., the volume changes in the image corresponding to the chest and abdomen are in opposite directions and cancel each other out). Due to blankets, covers, clothing, or even the patient's posture, this may not occur and a reduction in the respiratory waveform may only occur during paradoxical breathing associated with obstructive sleep apnea. Therefore, the above method may also be triggered if only a reduction in the respiratory waveform is detected.

FIG. 11 shows the airflow from a patient with obstructive sleep apnea and the corresponding PPG signal. The five apnea cycles in the figure correspond to major oscillations in the PPG waveform. Note, at this level of detail, individual PPG pulses are not distinguishable, rather only the gross behavior of the baseline is seen.

An additional signal that can be used to verify that an event is an apnea is the blood oxygen saturation (SpO2), detectable or estimatable by the pulse oximetry system. If the apnea (obstructive, central, or other) continues for long enough, a drop in SpO2 is noticed; such a drop (an absolute drop or relative drop) may indicate an apneic event. In some instances, rather than monitoring a drop in SpO2, a drop in SpO2 may be forecast. Using the SpO2 level may be useful in the scenarios where the respiratory waveform does not completely reduce to zero (as described above). An example method 1200 is shown in FIG. 12.

Figure 12:
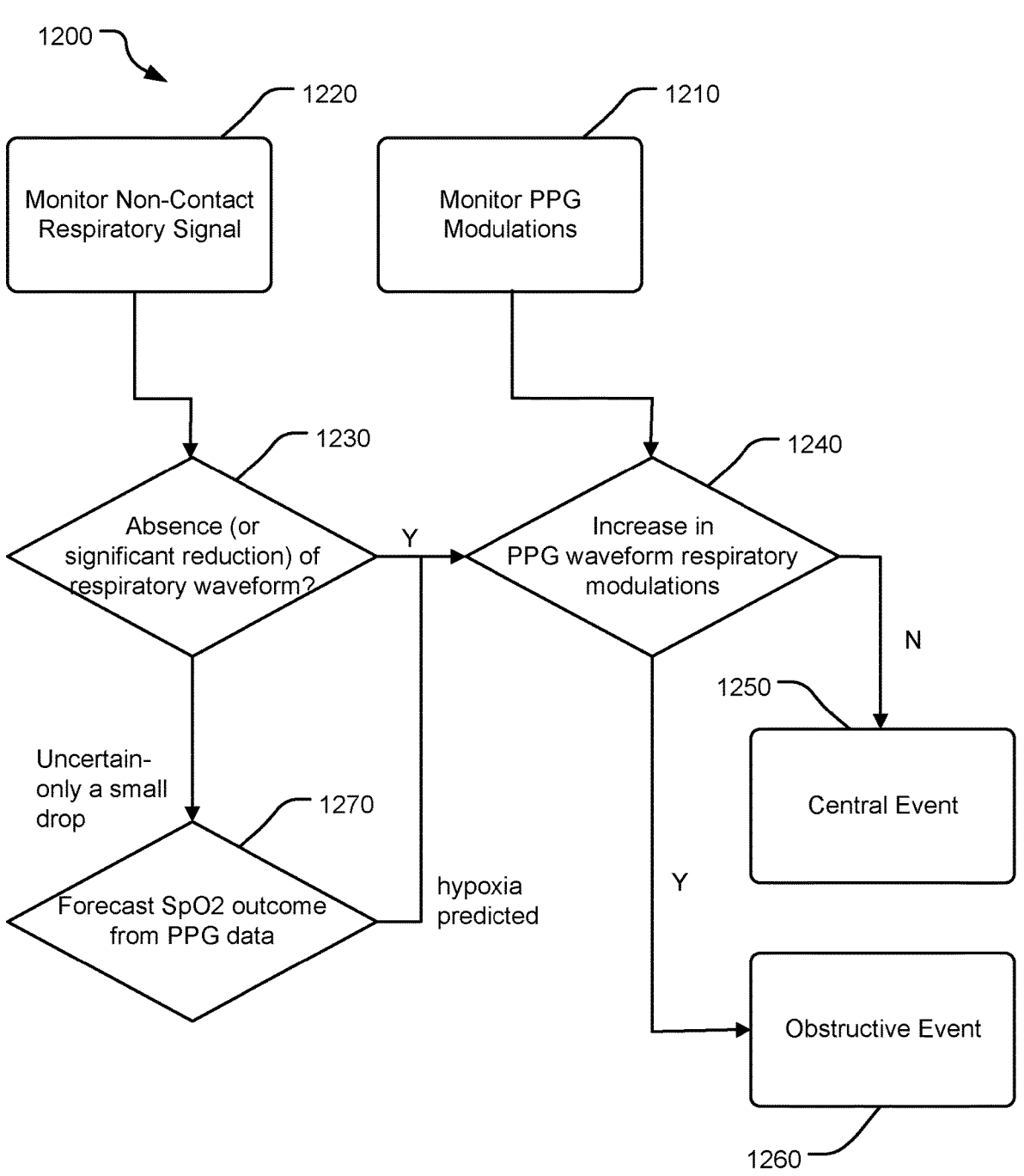
FIG. 12 is a flow chart of a stepwise method for estimating an apnea event.

In FIG. 12, in a first step 1210, PPG modulations are monitored with a pulse oximetry system. Simultaneously, subsequently, or before the step 1210, the respiratory signal from a non-contact patient monitoring system is monitored in step 1220. When an absence of, or reduction of, the respiratory waveform is detected in the step 1230, the results from the step 1210 are reviewed in step 1240 to determine if an increase in PPG waveform that corresponds to respiratory modulations was observed. If "no," the event is a central event in step 1250, but if "yes," the event is defined as an obstructive event in step 1260. However, if no absence of, or threshold-exceeding reduction of, the respiratory waveform is detected in the step 1230, for example, there is only a relatively small drop or reduction, leading to uncertainty, then in step 1270, a drop in SpO2 is forecast and hypoxia is predicted.

The above specification and examples provide a complete description of the structure and use of exemplary embodiments of the invention. The above description provides specific embodiments. It is to be understood that other embodiments are contemplated and may be made without departing from the scope or spirit of the present disclosure. The above detailed description, therefore, is not to be taken in a limiting sense. For example, elements or features of one example, embodiment or implementation may be applied to any other example, embodiment, or implementation described herein to the extent such contents do not conflict. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

The invention claimed is:

1. A method of identifying sleep apnea, the method comprising:

receiving, from a depth camera, a video signal comprising a patient in a field of view;

receiving, from a photoplethysmogram (PPG) sensor, a PPG signal of the patient;

extracting, from the video signal, depth information in the field of view;

calculating a respiratory parameter of the patient from the depth information;

detecting a reduction in amplitude of the respiratory parameter, the reduction being greater than a first threshold value;

in response to the detected reduction, defining an apnea event and triggering an alarm;

identifying, from the PPG signal, a PPG modulation comprising one or more of an amplitude modulation of the PPG signal, a baseline modulation of the PPG signal, and a frequency modulation of the PPG signal, the PPG modulation corresponding in time to the reduction;

identifying a presence or an absence of an increase in the PPG modulation, the increase being greater than a second threshold value;

upon identifying the presence of the increase in the PPG modulation, classifying the apnea event as an obstructive sleep apnea event; and upon identifying the absence of the increase in the PPG modulation, classifying the apnea event as a central sleep apnea event.

2. The method of claim 1, wherein the first threshold value is 25%.

3. The method of claim 1, wherein the second threshold value is 20%.

4. The method of claim 1, wherein defining the apnea event comprises detecting the reduction for at least 10 seconds.

5. The method of claim 1, wherein the respiratory parameter comprises one or both of respiratory rate and respiratory volume.

6. The method of claim 1, wherein the video signal comprises one or more of stereo images, IR image reflection intensity, and RGB reflection intensity.

7. The method of claim 1, wherein receiving the video signal occurs simultaneously with receiving the PPG signal.

8. The method of claim 1, further comprising monitoring a blood oxygen saturation (SpO2) level of the patient from the PPG signal.

9. The method of claim 1, wherein the video signal comprises image frames taken at greater than 60 frames per second.

10. The method of claim 1, further comprising displaying, on a display, a graphical representation of the apnea event.

11. The method of claim 1, further comprising outputting an image from the depth camera and superimposing a visualization of respiration on the image.

12. A method of detecting a sleep apnea event, the method comprising:

detecting, by a depth camera having a field of view, a depth signal comprising time-varying distances between the depth camera and a patient in the field of view;

calculating, from the depth signal, by a processor in communication with the depth camera, a movement of the patient;

deriving, from the movement, a respiratory parameter of the patient;

detecting a reduction in the respiratory parameter lasting at least a duration, the reduction being greater than a first threshold value;

defining the reduction as an apnea event;

receiving a photoplethysmogram (PPG) waveform of the patient from a pulse oximetry system;

extracting, from the PPG waveform, a PPG modulation comprising modulation of one or more of an amplitude of the PPG waveform, a baseline of the PPG waveform, and a frequency of the PPG waveform;

utilizing the PPG modulation to distinguish the apnea event as obstructive apnea or central apnea; and outputting an alarm indicating the apnea event.

13. The method of claim 12, wherein distinguishing the apnea event as obstructive apnea comprises detecting an increase in the PPG modulation.

14. The method of claim 12, wherein distinguishing the apnea event as central apnea comprises detecting no increase or a decrease in the PPG modulation.

15. The method of claim 12, wherein the respiratory parameter comprises one or both of respiratory rate and respiratory volume.

16. The method of claim 12, wherein the first threshold value is 25%.

17. The method of claim 12, wherein the duration is at least 10 seconds.

18. The method of claim 12, further comprising monitoring a blood oxygen saturation (SpO2) level of the patient with the pulse oximetry system.

19. The method of claim 12, further comprising identifying a steady-state amplitude of the respiratory parameter prior to the apnea event, and detecting the reduction in comparison to the steady-state amplitude.

20. The method of claim 12, further comprising outputting an image from the depth camera and superimposing a visualization of respiration on the image.

* * * * *